United States Patent
Kim et al.

(10) Patent No.: US 11,370,811 B1
(45) Date of Patent: Jun. 28, 2022

(54) (17-)-3-OXOANDROST-4-EN-17-YL DODECANOATE COMPOSITIONS AND METHODS OF PREPARATION AND USE

(71) Applicant: Lipocine Inc., Salt Lake City, UT (US)

(72) Inventors: Kilyoung Kim, West Jordan, UT (US); Mahesh V. Patel, Salt Lake City, UT (US); Nachiappan Chidambaram, Sandy, UT (US); Joel Frank, Sandy, UT (US)

(*) Notice: Subject to any disclaimer, the term of this patent is extended or adjusted under 35 U.S.C. 154(b) by 0 days.

(21) Appl. No.: 16/953,607

(22) Filed: Nov. 20, 2020

(51) Int. Cl.
*C07J 9/00* (2006.01)

(52) U.S. Cl.
CPC ........... *C07J 9/005* (2013.01); *C07B 2200/13* (2013.01)

(58) Field of Classification Search
CPC ............................. C07J 9/005; C07B 2200/13
See application file for complete search history.

(56) References Cited

U.S. PATENT DOCUMENTS

| | | |
|---|---|---|
| 8,865,695 B2 | 10/2014 | Giliyar et al. |
| 9,034,858 B2 | 5/2015 | Giliyar et al. |
| 9,498,485 B2 | 11/2016 | Patel et al. |
| 9,757,389 B2 | 9/2017 | Patel et al. |
| 2016/0184320 A1 | 6/2016 | Patel et al. |
| 2017/0035781 A1 | 2/2017 | Giliyar et al. |
| 2018/0125858 A1 | 5/2018 | Patel et al. |
| 2019/0275060 A1 | 9/2019 | Giliyar et al. |
| 2020/0046731 A1 | 2/2020 | Patel et al. |

OTHER PUBLICATIONS

Bhattacharya et al. (Brittain, ed. Polymorphism in Pharmaceutical Solids, 2009, p. 334.*
Boroweicki et al. (ARKIVOC, 2019, 6, pp. 288-305).*

* cited by examiner

*Primary Examiner* — Susanna Moore
(74) *Attorney, Agent, or Firm* — Michael R. Schramm

(57) ABSTRACT

Disclosed are bioavailable solid state (17-β)-3-Oxoandrost-4-en-17-yl dodecanoate compositions and methods of use in administration to mammals in need of thereof. The (17-β)-3-Oxoandrost-4-en-17-yl dodecanoate is preferably provided in a solid state crystalline form having a plurality of peaks corresponding to the peaks shown in FIG. 2, a plurality of crystallites ranging in size from about 40 nm to about 60 nm based as identified via powder x-ray diffraction spectra, and a melting point in the range of about 51° C. to about 63° C. The compositions may be provided in oral or injectable administration form for the treatment of conditions such as in need of testosterone therapy. An exemplary chemical structure of a (17-β)-3-Oxoandrost-4-en-17-yl dodecanoate composition disclosed herein is as follows:

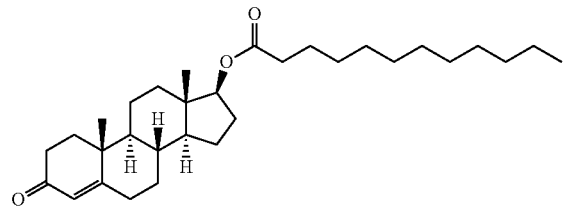

22 Claims, 4 Drawing Sheets

(17-)-3-OXOANDROST-4-EN-17-YL DODECANOATE COMPOSITIONS AND METHODS OF PREPARATION AND USE

FIELD OF THE INVENTION

Disclosed herein are solid state (17-β)-3-Oxoandrost-4-en-17-yl dodecanoate (see: https://pubchem.ncbi.nlm.nih.gov/compound/Dodecanoate), a novel ester of dodecanoic fatty acid, and its methods of pharmaceutical compositions suitable for pharmaceutical uses and administration to mammals (e.g., humans) in need of (17-β)-Hydroxy-4-Androsten-3-one.

BACKGROUND OF THE INVENTION

Various bioavailable solid state esters suitable for pharmaceutical uses and administration to mammals in need thereof are disclosed in the following US patents and applications, all of which are expressly incorporated herein in their entirety by reference: 8,865,695 filed Feb. 26, 2014 and issued Oct. 21, 2014, U.S. Pat. No. 9,034,858 filed May 31, 2012 and issued May 19, 2015, U.S. Pat. No. 9,498,485 filed Aug. 28, 2015 and issued Nov. 22, 2016, U.S. Pat. No. 9,757,389 filed Sep. 26, 2016 and issued Sep. 12, 2017, 2016/0184320 filed Aug. 28, 2015 and published Jun. 30, 2016, 2017/0035781 filed Jun. 22, 2016 and published Feb. 9, 2017, 2018/0125858 filed Aug. 8, 2017 and published May 10, 2018, 2019, 0275060 filed Aug. 6, 2018 and published Sep. 12, 2019, 2020/0046731 filed Feb. 12, 2019 and published Feb. 13, 2020 (the Patents).

Different solid state forms of an ester of an active pharmaceutical ingredient (API) or esterified active pharmaceutical ingredient (EAPI) may possess different properties that can provide a formulation, in which the EAPI is included, with specific advantages, for example, by facilitating better processing or handling characteristics, changing the dissolution profile in a favorable direction, or improving stability (polymorph as well as chemical stability) and shelf-life. These variations in the properties of different solid state forms may also translate to benefits to a final dosage form, for instance, by providing or contributing to improved bioavailability. Different solid state forms of an EAPI may also give rise to a variety of polymorphs or crystalline forms, which may in turn provide additional opportunities to assess variations in the properties and characteristics of a solid EAPI.

An important characteristic of EAPI is that its dissolution or release rate does not change substantially over time period. Changes in dissolution or release rate of EAPI over time period can result from otherwise identical products except for the solid state form (e.g., having the same EAPI, formulations components and amounts thereof), but can result in different pharmacokinetic properties which can change or alter the efficacy or safety of a drug product.

The stability of EAPI in pharmaceutical preparations (e.g., compositions and unit dosage forms) is also important. For example, if the EAPI changes physical form (e.g., crystal form or amount thereof) in a pharmaceutical composition or unit dosage form, this can also affect pharmacokinetic properties and therefore related safety and efficacy parameters.

To be useful, the solid state has to be stable. A number of examples of bulk drug substance and pharmaceutical compositions/dosage forms that have changed physical form are known in the literature and have resulted in substantial problems to patients receiving these drugs. A well-known example is ritonavir which underwent a change in crystal form resulting in the product failing dissolution tests and being pulled off the market for a period of time (see Morissette et al. Proc Natl Acad Sci USA. 2003 Mar. 4; 100(5):2180-4). Other high profile cases include the recall of batches of Neupro (rotigotine) due to the appearance of a new polymorph in 2008, recall of 1.5 million tablets of warfarin in 2010 due to concerns over 2-propanol levels, which potentially could affect API crystallinity, and in 2010 the recall of 60 million tablets of Avalide over concerns in variability in the amounts of the less soluble polymorph of irbesartan in 2010. See Lee et al. Annu. Rev. Chem. Biomol. Eng. 2011, 2, 259-280.

Absorption of any prodrug such as an ester derivative of an API (EAPI) needs to be managed to provide adequate and sustained levels of the API derived from EAPI in vivo without adding any safety issues associated with the ester or its metabolite. Solubility, release, dissolution and partitioning of EAPI in a particular solvent is a function of lipophilicity and is related to solid state characteristics e.g., the physical form of the drug substance such as crystal form, solvation, whether or not amorphous material is present, etc. Therefore, the solid state physical form is one of the key properties with respect to ease of manufacturing, storage, and performance of the EAPI for enabling safe and effective levels of API.

Esters of (17-β)-Hydroxy-4-Androsten-3-one, which themselves are not thought to be biological active, are known to be transformed to the biologically active molecule ((17-β)-Hydroxy-4-Androsten-3-one in vivo and other related metabolites like (17-β)-hydroxy-5α-androstan-3-one, and therefore can be used for treating patients in need of (17-β)-Hydroxy-4-Androsten-3-one treatment. However, inadequate solubility, release, dissolution, partitioning, and/or physical stability of the solid state of the EAPI can result in poor bioavailability of (17-β)-Hydroxy-4-Androsten-3-one, a useful hormone for the treatment of disease states related to need of (17-β)-Hydroxy-4-Androsten-3-one, such as e.g., male or female hypogonadism, lung disease, or liver disease.

Several prodrug esters of (17-β)-Hydroxy-4-Androsten-3-one have been reported in the literature (Gooren L J, Front Horm Res. 2009; 37:32-5). However, in addition to overcoming solubility challenges with esters of (17-β)-Hydroxy-4-Androsten-3-one, adequate absorption and conversion rate into the parent drug remain an important design element in preparing and identifying solid state esters of (17-β)-Hydroxy-4-Androsten-3-one. Approaches to date have failed to disclose or adequately characterize specific solid state (17-β)-3-Oxoandrost-4-en-17-yl dodecanoate used for ease in development of pharmaceutical compositions.

Steroids including steroid esters, such as testosterone and testosterone esters, are known to exhibit different solid state forms that have different properties including dissolution, bioavailability and absorption (See e.g., Ballard B E, Biles J, Steroids, 1964; 4: 273; Bouche R, Draguet-Brughmans M, J Pharm Belg, 1977; 32: 347; Carless et al. Journal of Pharmacy and Pharmacology Volume 20, Issue 8, pages 630-638, August 1968; Borka & Haleblian (1990) Acta Pharm. Jugosl. 40:71-94).

Esterification of testosterone with dodecanoic acid (lauric acid) are more suitable and preferred for therapy since lauric acid is a saturated medium chain fatty acid (MCFA) with 12 carbon atoms associated with certain health benefits. There is a need for stable and bioavailable solid state forms of (17-β)-3-Oxoandrost-4-en-17-yl dodecanoate, a candidate of new drug products on male or female hypogonadism, lung disease, sarcopenia (see: https://society-scwd.org/sarcopenia/), cachexia (see: https://society-scwd.org/cachexia/), muscle wasting (see: https://:society-scwd.org/muscle-wasting/), or liver disease that would be suitable for use in treatment of subjects in need of (17-β)-Hydroxy-4-Androsten-3-one.

SUMMARY OF THE INVENTION

It was found that not all solid state forms of the dodecanoate ester derivative of ((17-β)-Hydroxy-4-Androsten-3-one are alike and suitable for treatment of mammals in need of (17-β)-Hydroxy-4-Androsten-3-one. It was found that a specific solid state dodecanoate ester derivative of (17-β)-Hydroxy-4-Androsten-3-one, wherein at least 0.001% (e.g., at least 0.01, 0.1 1.0 or 10%) of the solid state (17-β)-3-Oxoandrost-4-en-17-yl dodecanoate dissolves in 1000 mL 8% Triton X100 containing aqueous solution in 30 minutes in a USP Type 2 apparatus at 37° C. at 100 rpm, are more suitable for administering to a human (e.g., treating or preventing a disease, condition or disorder).

Additionally, it was found that compositions of the selected solid forms described herein are adequately bioavailable. In one embodiment, a composition for administration to a human subject in need of ((17-β)-Hydroxy-4-Androsten-3-one therapy is provided: e.g., the composition comprising or made from a) a solid state of (17-β)-3-Oxoandrost-4-en-17-yl dodecanoate and b) a pharmaceutically acceptable carrier, wherein upon oral administration of the solid state of (17-β)-3-Oxoandrost-4-en-17-yl dodecanoate to the human subject, at least about 0.1% 0.5%, 1%, 2%, 3%, 5%,8% or 10% of the (17-β)-Hydroxy-4-Androsten-3-one (testosterone) equivalent dose is bioavailable to the human subject.

Thus, in one embodiment, a solid state EAPI which is (17-β)-3-Oxoandrost-4-en-17-yl dodecanoate is provided. The solid state (17-β)-3-Oxoandrost-4-en-17-yl dodecanoate is crystalline. In a specific aspect, the crystalline solid state (17-β)-3-Oxoandrost-4-en-17-yl dodecanoate is a crystal form substantially free of other non-crystal forms. In another specific aspect, the crystalline solid state (17-β)-3-Oxoandrost-4-en-17-yl dodecanoate described herein is substantially free of amorphous forms.

The solid state (17-β)-3-Oxoandrost-4-en-17-yl dodecanoate provided herein has a characteristics of particle size distribution. In specific aspects, the particle sizes of the solid state (17-β)-3-Oxoandrost-4-en-17-yl dodecanoate are less than 200 nm ("nanometer"), from 200 to 500 nm, from 500 to 1000 nm, from 1 to 50 μm ("micrometer"), from 50 to 250 μm, from 250 to 500 μm, from 500 to 1000 μm, or greater than 1000 μm. In another aspect, the solid state (17-β)-3-Oxoandrost-4-en-17-yl dodecanoate has a $d_{50}$ of greater than 1000 μm, from 355 to 1000 μm, from 180 to 355 μm, from 125 to 180 μm, 90 to 125 μm, from 1 to 90 μm, or less than 1 μm. In another related aspect, the solid state (17-β)-3-Oxoandrost-4-en-17-yl dodecanoate has a $D_{10}$, $D_{50}$, or $D_{90}$ that is less than 200 nm, from 200 to 500 nm, from 500 to 1000 nm, from 1 to 50 μm, from 50 to 250 μm, from 250 to 500 μm, from 500 to 1000 μm, or greater than 1000 μm. In one particular aspect, the solid state (17-β)-3-Oxoandrost-4-en-17-yl dodecanoate having a characteristics of particle size distribution or size characteristics is crystalline. In another particular aspect, the solid state (17-β)-3-Oxoandrost-4-en-17-yl dodecanoate having a characteristics of particle size distribution or size characteristics is a crystal form substantially free of other non-crystalline forms.

Pharmaceutical compositions provided herein comprise or are prepared from a solid state (17-β)-3-Oxoandrost-4-en-17-yl dodecanoate as described in the paragraphs above. For example, the pharmaceutical composition is prepared from or comprises a solid state (17-β)-3-Oxoandrost-4-en-17-yl dodecanoate and one or more pharmaceutically acceptable excipients, carriers, or additives. The pharmaceutical composition described herein can comprise or be prepared from crystalline solid state (17-β)-3-Oxoandrost-4-en-17-yl dodecanoate. In some aspects, the pharmaceutical composition comprises or is prepared from solid state (17-β)-3-Oxoandrost-4-en-17-yl dodecanoate, where is not-milled or is milled, micronized or nanosized. In specific aspects, the pharmaceutical composition comprises or is prepared from solid state (17-β)-3-Oxoandrost-4-en-17-yl dodecanoate wherein the particle size is less than 200 nm, from 200 to 500 nm, from 500 to 1000 nm, from 1 to 50 μm, from 50 μm to 250 μm, from 250 μm to 500 μm, from 500 μm to 1000 μm, or greater than 1000 μm. In another aspect, the pharmaceutical composition comprises or is prepared from solid state (17-β)-3-Oxoandrost-4-en-17-yl dodecanoate having a $d_{50}$ of greater than 1000 μm, from 355 to 1000 μm, from 180 to 355 μm, from 125 to 180 μm, from 90 to 125 μm, from 1 to 90 μm, or less than 1 μm. In another related aspect, the pharmaceutical composition comprises or is prepared from solid state (17-β)-3-Oxoandrost-4-en-17-yl dodecanoate having a $D_{10}$, $D_{50}$, or $D_{90}$ that is less than 200 nm, from 200 to 500 nm, from 500 to 1000 nm, from 1 to 50 μm, from 50 to 250 μm, from 250 to 500 μm, from 500 to 1000 μm, or greater than 1000 μm. In some specific aspects, the pharmaceutical composition of solid state (17-β)-3-Oxoandrost-4-en-17-yl dodecanoate is formulated for topical, enteral or parenteral administration. In some aspects, the pharmaceutical composition of solid state (17-β)-3-Oxoandrost-4-en-17-yl dodecanoate is formulated for buccal, sublingual, or sublabial administration. In some specific aspects, the pharmaceutical composition of solid state (17-β)-3-Oxoandrost-4-en-17-yl dodecanoate is formulated for nasal, rectal or vaginal administration. In some specific aspects, the pharmaceutical composition of solid state (17-β)-3-Oxoandrost-4-en-17-yl dodecanoate is formulated for intravenous, subcutaneous, intramuscular, intradermal, intraspinal, intrathecal, or intra-arterial administration. In some specific aspects, the pharmaceutical composition of solid state (17-β)-3-Oxoandrost-4-en-17-yl dodecanoate is formulated as liquid, solution, suspension, dispersion (see: https://en.wikipedia.org/wiki/Depression_(chemistry)), solid, semi-solid, gel, lotion, paste, foam, spray, suspension, dispersion, syrup, or ointment. In some specific aspects, the pharmaceutical composition of solid state (17-β)-3-Oxoandrost-4-en-17-yl dodecanoate is formulated as a tincture, patch, injectable, or oral dosage form. In some aspects, the pharmaceutical composition of solid state (17-β)-3-Oxoandrost-4-en-17-yl dodecanoate comprises solubilized or partially solubilized (17-β)-3-Oxoandrost-4-en-17-yl dodecanoate. In one aspect, the pharmaceutical composition or unit dosage form is suitable for oral administration (e.g., capsule or tablet).

Provided herein are pharmaceutically compositions or unit dosage forms comprising or prepared from solid state (17-β)-3-Oxoandrost-4-en-17-yl dodecanoate as described in the paragraphs above.

Additionally, described herein are methods of using solid state (17-β)-3-Oxoandrost-4-en-17-yl dodecanoate for pharmaceutical compositions wherein can treat males or females in need of (17-β)-Hydroxy-4-Androsten-3-one (testosterone).

DETAILED DESCRIPTION

Figure 1:
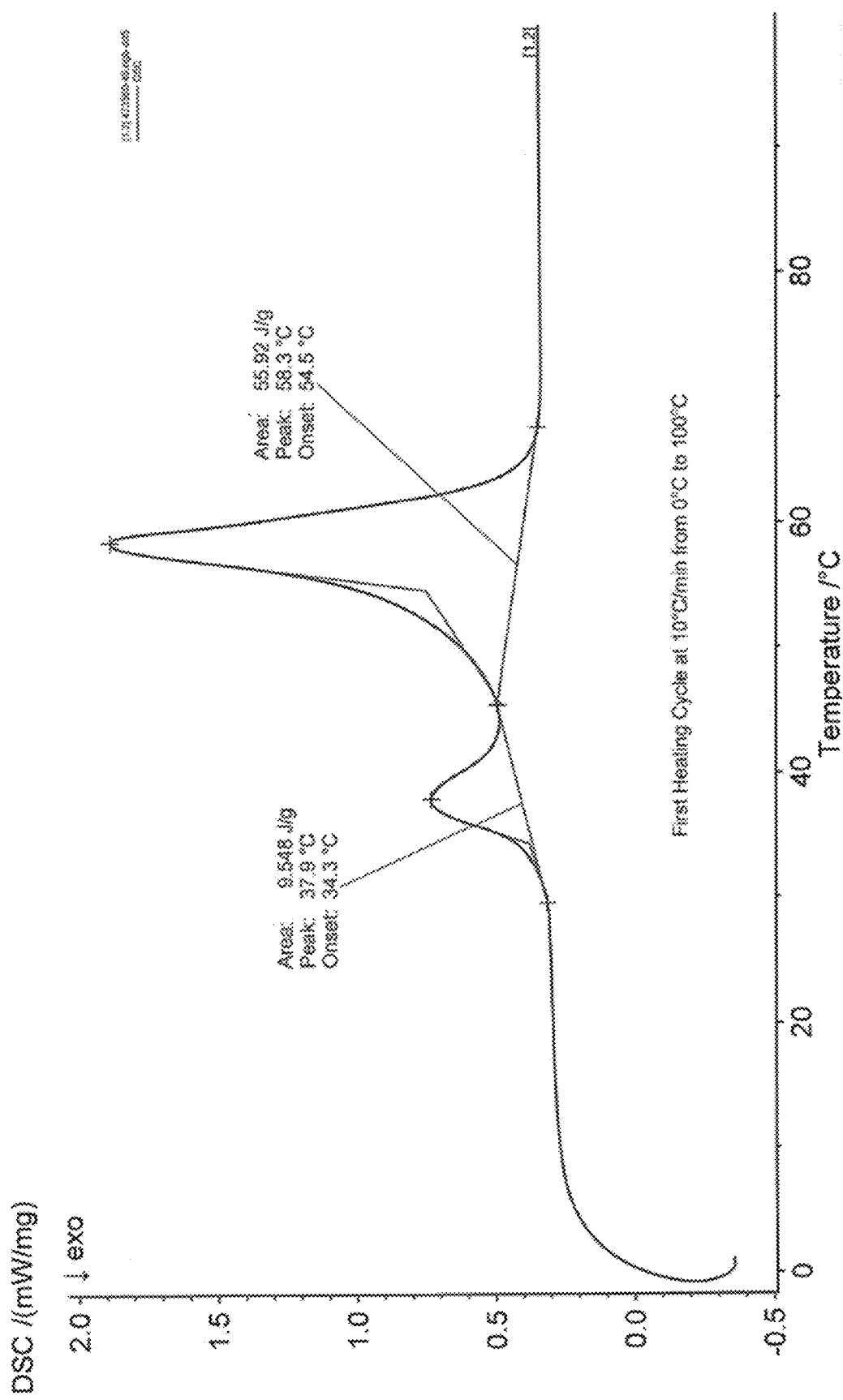
FIG. 1 shows a first heat cycle heat enthalpy change plot for a solid state form of (17-β)-3-Oxoandrost-4-en-17-yl dodecanoate measured by differential scanning calorimetry as disclosed herein.

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting.

Furthermore, the described features, structures, or characteristics can be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein, but are merely representative thereof.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

As used herein, the terms "treat," "treatment," or "treating" and the like refers to administration of a therapeutic agent to a pathogen-infected subject who is either asymptomatic or symptomatic. In other words, "treat," "treatment," or "treating" can refer to reducing, ameliorating or eliminating symptoms associated with a condition present in an infected subject.

As used herein, "androgen receptor agonists" refers to compounds, molecules, or agents such as testosterone that bind and activate an androgen receptor. Examples of androgen receptor agonists include, but are not limited to, dihydrotestosterone, mibolerone, testosterone, alkylated testosterone, derivatives of testosterone esters, methyltrienolone, oxandrolone, nandrolone and fluoxymesterone. Where appropriate, fatty acid esters of these androgen receptor agonists can be used herein accordingly.

As used herein, "testosterone ester" refers to testosterone esterified with a fatty acid. Exemplary testosterone esters include without limitation testosterone undecanoate, testosterone decanoate, testosterone dodecanoate, testosterone tridecanoate, testosterone decanoate, testosterone enanthate, testosterone palmitate, testosterone cypionate, and testosterone propionate.

As used herein, "testosterone agent" refers to an active pharmaceutical agent that produces a physiologic action or effect of testosterone in-vivo. Examples of testosterone agents are found throughout the present application. One example of a testosterone agent is testosterone (T). Another example is a testosterone ester, such as testosterone undecanoate or testosterone tridecanoate.

As used herein, the terms "therapeutic agent," "active agent," and the like can be used interchangeably and refer to agent that can have a beneficial or positive effect on a subject when administered to the subject in an appropriate or effective amount. In one aspect, the therapeutic or active agent can be an androgenic steroid. The terms "additional active agent," "supplemental active agent," "secondary active agent," and the like can be used interchangeably and refer to a compound, molecule, or material other than an androgenic steroid that has physiologic activity when administered to a subject in an effective amount.

As used herein, the terms "formulation" and "composition" are used interchangeably and refer to a mixture of two or more compounds, elements, or molecules. In some aspects, the terms "formulation" and "composition" may be used to refer to a mixture of one or more active agents with a carrier or other excipients. Furthermore, the term "dosage form" can include one or more formulation(s) or composition(s) provided in a format for administration to a subject. For example, an "oral dosage form" can be suitable for administration to a subject's mouth. A "topical dosage form" can be suitable for administration to a subject's skin by rubbing, etc.

As used herein, a "subject" refers to an animal. In one aspect the animal may be a mammal. In another aspect, the mammal may be a human.

As used herein, "in need of treatment" refers to a subject that has a disease or is suspected of having the disease according to various diagnostic criteria typically used in practice, or desires treatment or is indicated for treatment. Thus, "in need of treatment" can include the step of identifying a subject in need of treatment.

As used herein, "identifying a subject in need of treatment" can include the step of obtaining a biological sample from the subject and determining the level of one or more biomarkers as described herein (RT-PCR detection of a virus gene), assessing a biological sample obtained from said subject, performing an imaging analysis on the subject, assessing one or more clinical characteristics of said subject (e.g., assessing symptoms or overt symptoms), or a combination thereof.

As used herein, an "acute" condition refers to a condition that can develop rapidly and have distinct symptoms needing urgent or semi-urgent care. By contrast, a "chronic" condition refers to a condition that is typically slower to develop and lingers or otherwise progresses over time. Some examples of acute conditions can include without limitation, an asthma attack, bronchitis, a heart attack, pneumonia, and the like. Some examples of chronic conditions can include without limitation, arthritis, diabetes, hypertension, high cholesterol, and the like.

The terms "serum testosterone" or "serum (17-β)-Hydroxy-4-Androsten-3-one levels," "serum T levels," "serum testosterone concentration," "plasma testosterone concentration," "testosterone concentration in the blood," and "serum testosterone concentration," are used interchangeably and refer to the "total" serum testosterone concentration which is the sum of the bioavailable testosterone including free and bound testosterone fractions or concentrations. As with any bioanalytical measure, for increased consistency, the method employed to measure initial serum testosterone levels may be consistent with the method used to monitor and re-measure serum testosterone levels during clinical testing and testosterone therapy for a subject. Unless otherwise stated, "testosterone concentration" refers to serum total testosterone concentration.

Average serum testosterone concentrations can be determined using methods and practices known in the art. For example, the average baseline plasma testosterone concentration of a human male is the arithmetic mean of the total plasma testosterone concentration determined on at least two consecutive time points that are reasonably spaced from each other, for example from about 1 hour to about 168 hours apart. In a particular case, the plasma testosterone concentration can be determined on at least two consecutive times that are about 12 hours to about 48 hours apart. In another particular method, the plasma testosterone concentration of the human male can be determined at a time between about 5 o'clock and about 11 o'clock in the morning. Further, the plasma testosterone concentration can be the determined by standard analytical procedures and methods available in the art, such as for example, automated or manual immunoassay methods, liquid chromatography or liquid chromatography-tandem mass spectrometry (LC-MSMS) etc.

As use herein with respect to physiologic levels of a given substance, the term "baseline" refers to a level or concentration of the substance in a subject prior to administration of an active agent. For example, the baseline level of serum testosterone in a subject would the subject's testosterone serum level prior (e.g. just prior) to the commencement of testosterone administration or therapy.

As used herein, "free testosterone serum concentration", refers to the fraction of total testosterone that is not bound to a protein e.g., SHBG (see: https://en.wikipedia.org/wiki/Sex_hormone-binding_globulin) or albumin. In some aspects of the methods described herein, free testosterone serum concentrations are used instead of serum total testosterone concentrations. For example, a subject can appear to have total serum testosterone levels in the normal range, but can be still considered testosterone deficient based on free testosterone levels. It should be understood that as used herein, the term testosterone serum levels or concentrations can provide express support for free testosterone serum concentrations, unless the context or recitation clearly dictates otherwise.

The term "oral administration" represents any method of administration in which an active agent can be administered by swallowing, chewing, or sucking of the dosage form. Oral administration can be intended for enteral delivery of an active agent or transmucosal delivery of the active agent. In some embodiments, the composition of the current inventions can be admixed with food or drink prior to being orally consumed.

As used herein, a "dosing regimen" or "regimen" such as an "initial dosing regimen" or "starting dose" or a "maintenance dosing regimen" refers to how, when, how much, and for how long a dose of the compositions of the present invention can be administered to a subject. For example, an initial or starting dose regimen for a subject may provide for a total daily dose of from about 15 mg to about 1500 mg administered in two divided doses at least 12 hours apart (e.g. once with breakfast and once with dinner) with meals repeated daily for 30 days.

As used herein, "daily dose" refers to the amount of active agent (e.g. a testosterone ester) administered to a subject over a 24-hour period of time. The daily dose can be administered one or more administrations during the 24-hour period. In one embodiment, the daily dose provides for two administrations in a 24-hour period. With this in mind, an "initial dose" or initial daily dose" refers to a dose administered during the initial regimen or period of a dosing regimen.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein "single unit" when used to describe dosing of a subject refers to the dosage form being a single dosage form, e.g. a single tablet, capsule, pump or squirt of gel or solution, etc. In contrast, "multiple unit" when used to describe dosing of a subject refers to the dosage including two or more dosage forms, e.g. 2 capsules, 3 tablets, 2-4 pumps or squirts, etc. It is noteworthy that multiple unit dosage forms generally will be the same type of dosage forms (i.e. tablet or capsule) but are not required to be the same dosage form type.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term, like "comprising" or "including," in the written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "worse," "higher," "lower," "enhanced," "improved," "maximized," "minimized," and the like refer to a property of a device, component, composition, biologic response, biologic status, or activity that is measurably different from other devices, components, compositions, biologic responses, biologic status, or activities that are in a surrounding or adjacent area, that are similarly situated, that are in a single device or composition or in multiple comparable devices or compositions, that are in a group or class, that are in multiple groups or classes, or as compared to an original (e.g. untreated) or baseline state, or the known state of the art. For example, a composition that "increases" testosterone serum levels provides a testosterone serum level in a subject that is elevated as compared to a serum level at a previous point in time, such as a baseline level (e.g. prior to treatment), or as compared to an earlier treatment with a different (e.g. lower dose).

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

The term "API" refers to active pharmaceutical ingredient or drug and means (17-β)-Hydroxy-4-Androsten-3-one (also known as testosterone) which is considered the biologically active agent for the purpose of this disclosure. It is noted that (17-β)-3-Oxoandrost-4-en-17-yl dodecanoate can be converted in vivo to (17-β)-hydroxy-5α-androstan-3-one (directly or via the corresponding ester) which is also biological activity as well as other metabolites. The term "EAPI" means an ester of (17-β)-Hydroxy-4-Androsten-3-one, a prodrug of the biologically active agent. It is understood that the EAPI can also have biological activity without cleavage of the ester, but for the purpose of this invention the API is considered the pharmacological agent, which is (17-β)-Hydroxy-4-Androsten-3-one (testosterone).

As used herein, the term $AUC_{t1-t2}$ is the area under the curve of a plasma-versus-time graph determined for the analyte from the time "t1 to t2" wherein t1 and t2 are times (in hours) post dosing. For Example, t1 could be 1 hour and t2 could be 2 hours post dose.

As used herein, the term "$C_{avg}$," "$C_{ave}$," or "C-average" are used interchangeably and determined as the mean values obtained from $AUC_{t1-t2}$ divided by the time period ($|t1-t2|$). For example, $C_{avg\ t0-t8}$ is the average plasma concentration over a period of 8 hours from t1=0 to t2=8 hours post-dosing determined by dividing the $AUC_{t0-t8}$ value by 8 hours. Similarly, $C_{avg\ t0-t12}$ is the average plasma concentration over a period of 12 hours post-dosing determined by dividing the $AUC_{t0-t12}$ value by 12 hours (t1=0 and t2=12). Similarly, $C_{avg\ t12-t24}$ is the average plasma concentration over a period of 12 hours post-dosing determined by dividing the $AUC_{t12-t24}$ value by 12 hours (t1=12 and t2=24); $C_{avgt0-t24}$ is the average plasma concentration over a period of 24 hours post-dosing determined by dividing the $AUC_{t0-t24}$ value by 24 hours (t1=0 and t2=24), and so on. Unless otherwise stated, all $C_{avg}$ values are considered to be $C_{avg\ t0-t24}$ and unless otherwise stated, all the time values are expressed in hours (h). For example, the term $C_{avg\ t0-t24}$ denotes $C_{avg}$ from time zero (0) to 24 hours post dosing.

As used herein, "$C_t$" refers to the serum concentration of testosterone at time "t" after administration of the dosage of the current invention. The time "t" is generally in hours post administration, unless otherwise specified. For example, a $C_t$ of "$C_{(-2\ to\ 0)}$" refers to serum testosterone concentration measured in sample collected between the time of about 2 hours before and just immediately prior to dosage administration to the subject tested. Similarly, $C_t$ of "$C_{(2\ to\ 4)}$" refers to serum testosterone concentration measured in sample collected between the time of about 2 hours and 4 hours after administration of a dosage to the subject tested.

As used herein, the term (17-β)-Hydroxy-4-Androsten-3-one refers to a chemical having an IUPAC name of (8R,9S,10R,13S,14S,17S)-17-Hydroxy-10,13-dimethyl-1,2,6,7,8,9,11,12,14,15,16,17-dodecahydrocyclopenta[a]phenanthren-3-one and a CAS number of 58-22-0. (17-β)-3-Oxoandrost-4-en-17-yl dodecanoate generically refers to compounds having the (17-β)-Hydroxy-4-Androsten-3-one structure but the hydroxyl group at the 17$^{th}$ carbon site on the testosterone structure is esterified with lauric acid (e.g., 12-carbon chain saturated alkanoic acid). For example, (8R,9S,10R,13S,14S,17S)-10,13-dimethyl-3-oxo-1,2,6,7,8,9,11,12,14,15,16,17-dodecahydrocyclopenta[a]phenanthren-17-yl dodecanoate is the IUPAC name for (17-β)-Hydroxy-4-Androsten-3-one esterified with a straight chain saturated 12 carbon long alkanoic acid called lauric acid. Dodecanoic acid, alternatively named lauric acid as well, is the IUPAC name for the saturated alkanoic acid having CAS number 143-07-7. In a more specific aspect, (17-β)-3-Oxoandrost-4-en-17-yl dodecanoate refers to those of (17-β)-3-Oxoandrost-4-en-17-yl laurate specifically disclosed herein. In one specific aspect, it refers to the dodecanoic (17-β)-Hydroxy-4-Androsten-3-one ester (referred to herein as (17-β)-3-Oxoandrost-4-en-17-yl dodecanoate, (17-β)-3-Oxoandrost-4-en-17-yl laurate, or the dodecanoic ester of (17-β)-Hydroxy-4-Androsten-3-one and the such (CAS No. 59232-78-9)). (17-β)-3-Oxoandrost-4-en-17-yl dodecanoate has the following chemical structure as shown in Exhibit 1:

Exhibit 1

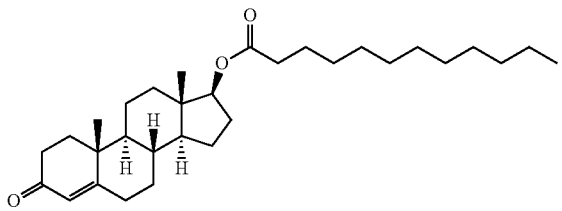

Solid state (17-β)-3-Oxoandrost-4-en-17-yl dodecanoate can exist in different crystalline forms as well as in non-crystalline forms. A non-crystalline solid form is referred to herein as an "amorphous form", which is a disordered arrangement of (17-β)-3-Oxoandrost-4-en-17-yl dodecanoate molecules. Different crystalline forms of (17-β)-3-Oxoandrost-4-en-17-yl dodecanoate arise from different packing of the (17-β)-3-Oxoandrost-4-en-17-yl dodecanoate molecules in the solid state, resulting in different crystal symmetries and/or unit cell parameters. Crystalline forms are identified or characterized by any suitable methods, e.g., x-ray diffraction (see, e.g., Remington's Pharmaceutical Sciences, 18th ed., Mack Publishing, Easton Pa., p 173 (1990); The United States Pharmacopeia, 23rd ed., pp. 1843-1844 (1995)). Such different crystalline forms are referred to herein as "polymorphic forms" or "non-solvated forms", which mean that they are essentially free of residual solvents, e.g., organic solvents. If the substances incorporate stoichiometric or non-stoichiometric amounts of water ("hydrate" as used herein), or any other solvent ("solvate" as used herein), in the crystal structure, these are referred to herein as a "pseudopolymorphic form."

The term "amorphous form" as used herein in connection with solid state refers to a non-crystalline solid form (i.e., not in a crystalline form), which is a disordered arrangements of (17-β)-3-Oxoandrost-4-en-17-yl dodecanoate molecules. Typically, an amorphous solid state (17-β)-3-Oxoandrost-4-en-17-yl dodecanoate has no long-range periodic molecular packing structure as determined by Powder X-ray Diffraction ("PXRD" or "XRD"). The XRD pattern of amorphous (17-β)-3-Oxoandrost-4-en-17-yl dodecanoate appears as a halo with no distinctive peaks. Amorphous forms for some compounds can be obtained by a number of methods known in the art, including, but not limited to, heating, melt cooling, rapid melt cooling, solvent evaporation, rapid solvent evaporation, desolvation, sublimation, grinding, cryo-grinding, spray-cooling or freeze-drying.

The term "crystal", "crystallite", or "crystalline" as used herein refers to a solid structure, typically formed by a solidification or crystallization, that generally has an ordered molecular packing structure (characteristic shapes and cleavage planes formed by the arrangement of molecules in a pattern referred to as a "lattice"). In an aspect, a number of crystallites agglomerate and then form any grains, which can be packed to form any particles. That is, particle size is greater than grain size, which is greater than any crystal size.

The term "seeding" as used herein refers to starting or promoting a crystallization event using a small amount of materials.

As used herein, the term "Triton X100" or Triton "X-100" is a non-ionic detergent and refers to a composition as known as polyethylene glycol p-(1,1,3,3-tetramethylbutyl)-phenyl ether, octyl phenol ethoxylate, polyoxyethylene octyl phenyl ether, 4-octylphenol polyethoxylate, Mono 30, TX-100, t-octylphenoxypolyethoxyethanol, or Octoxynol-9 and associated with CAS NO. 9002-93-1.

A "pharmaceutical composition" or "formulation" as used herein refers to a composition comprising or prepared from a solid state (17-β)-3-Oxoandrost-4-en-17-yl dodecanoate and one or more pharmaceutically acceptable carriers, excipients, or additives. Moreover, an exemplary composition may be any of the compositions taught in the Patents. A "unit dosage form" as used herein refers to a medicament prepared from or comprising a pharmaceutical composition and includes tablets, capsules, caplets, gelcaps, ampoules, suspensions, solutions, gels, dispersions and other dosage units typically associated with parenteral, enteral, topical or other forms of administration of (17-β)-3-Oxoandrost-4-en-17-yl dodecanoate to a subject in need thereof.

A "pharmaceutically acceptable carrier", "pharmaceutically acceptable excipient", "pharmaceutically acceptable additive", or similar term refers to one or multiple components or ingredients that are acceptable (1) as being compatible with the other ingredients in compositions or formulations comprising (17-β)-3-Oxoandrost-4-en-17-yl dodecanoate and (2) are not deleterious nor overly deleterious to a subject to whom the composition or formulation is to be administered. Excipients include any of the excipients disclosed in the Patents.

Carriers (e.g., pharmaceutically acceptable excipients or additives) and methods of preparing oral pharmaceutical compositions comprising (17-β)-3-Oxoandrost-4-en-17-yl dodecanoate are available to the skilled artisan in view of this application which typically involve a specific solid state form of the (17-β)-3-Oxoandrost-4-en-17-yl dodecanoate.

Reference will now be made in detail to specific embodiments of the invention. While the invention will be described in conjunction with such embodiments, it will be understood that it is not intended to limit the invention to those embodiments. To the contrary, it is intended to cover alternatives, variants, modifications, and equivalents as may be included within the spirit and scope of the invention as defined by the appended claims.

Solid State Forms of (17-β)-3-Oxoandrost-4-en-17-yl dodecanoate

The specific solid state forms of (17-β)-3-Oxoandrost-4-en-17-yl dodecanoate disclosed herein have one or more advantageous properties compared to other forms such as chemical or polymorphic purity, increased crystallinity, flowability, solubility, dissolution rate, bioavailability, morphology or crystal habit, specific surface and pycnometric density, bulk/tap density, stability (e.g., such as chemical stability as well as thermal and mechanical stability with respect to polymorphic conversion), stability towards hydration and/or storage stability, a lower degree of hygroscopicity, low content of residual solvents and advantageous processing and handling characteristics such as compressibility and bulk density. Specific solid state forms of (17-β)-3-Oxoandrost-4-en-17-yl dodecanoate are provided herein.

(17-β)-3-Oxoandrost-4-en-17-yl dodecanoate can be prepared by a number of synthetic routes (as well as other corresponding esters in an analogous fashion). For example, (17-β)-3-Oxoandrost-4-en-17-yl dodecanoate is prepared under the corresponding alcohol via an esterification reaction with (17-β)-Hydroxy-4-Androsten-3-one and an activated fatty acid of n-dodecanoic acid (IUPAC name as lauric acid, CAS number 143-07-7): e.g., a lauroyl chloride or anhydride, in a suitable solvent under suitable conditions to produce the product (e.g., pyridine as a catalyst of esterification). In one aspect, the (17-β)-Hydroxy-4-Androsten-3-one (testosterone) is prepared from a phytosterol or cholesterol or any other suitable starting material. The product is worked up via any number of techniques. For example, the product is dissolved in a solvent (e.g., organic solvent such as heptanes or any other solvent); washed successively with e.g., cold water (2×), 0.05 N NaOH, saturated NaHCO$_3$ (2×), water, brine, then dried over anhydrous Na$_2$SO$_4$ (~50 g), followed by drying process (e.g., rotavap/T$_{bath}$<30° C.). Without wishing to be bound by theory, the inventors have unexpectedly found that crystallization or recrystallization of (17-β)-3-Oxoandrost-4-en-17-yl dodecanoate provides solid state forms with one or more advantageous properties as described herein.

Thus, according to one embodiment, an example of recrystallized or crystallized solid state (17-β)-3-Oxoandrost-4-en-17-yl dodecanoate is provided here. According to this embodiment, (17-β)-3-Oxoandrost-4-en-17-yl dodecanoate is dissolved in a solvent (e.g., heptane) and allowed to crystallize or recrystallize or after a first crystallization is transferred to another solvent and allowed to crystallize or recrystallize. The crystalline mass can be isolated (e.g., filtered by suction), optionally washed (e.g., with water), optionally dried (e.g., over phosphorous pentoxide) and optionally re-crystallized from another solvent e.g., oleic acid, hexane, heptanes, etc. In one aspect, the solvent (for crystallization or recrystallization) is an alcohol (e.g., ethanol, methanol, or propanol), fatty acid (e.g., oleic acid, linoleic acid, or linoeladic acid), alkane (e.g., hexane, heptane, pentane, or halogenated alkane), oil (e.g., vegetable oil, castor oil, or hydrogenated oil), or any other suitable solvent (e.g., pyridine, benzene, or toluene). In this context, a solvent refers to a liquid in which (17-β)-3-Oxoandrost-4-en-17-yl dodecanoate is soluble.

Crystalline forms of a substance can be obtained by a number of techniques, as is known in the art. Exemplary techniques for obtaining, producing, or manufacturing crystalline forms of (17-β)-3-Oxoandrost-4-en-17-yl dodecanoate include melt recrystallization, melt cooling, solvent recrystallization, recrystallization in confined spaces such as in nanopores or capillaries, recrystallization on surfaces or templates such as on polymers, recrystallization in the presence of additives, such as co-crystal counter-molecules, desolvation, dehydration, rapid evaporation, rapid cooling, slow cooling, vapor diffusion, sublimation, grinding and solvent-drop grinding.

Typically, specific crystalline forms of active pharmaceutical ingredients (API) (e.g., testosterone esters) can be distinguished from each other by one or more physical or chemical properties such as rate of dissolution, infrared or Raman spectroscopy, x-ray diffraction techniques (e.g., single crystal and powder diffraction techniques), solid state-NMR (SS-NMR) (see: https://en.wikipedia.org/wiki/Soild-state_nuclear_magnetic_resonance), thermal techniques such as melting point, differential thermal analysis (DTA) (see: https://en.wikipedia.org/wiki/Differential_thermal_analysis), differential scanning calorimetry (DSC) (see: https://en.wikipedia.org/wiki/Differential_scanning_calorimetry), thermal gravimetric analysis (TGA) (see: https://en.wikipedia.org/wiki/Thermogravimetric_anaiysis) and other methods as disclosed elsewhere in the specification or available to the skilled artisan. Other methods to characterize or distinguish a pseudopolymorphic form from another isostructural polymorphs, pseudopolymorphs, desolvates or anhydrates include elemental analysis, Karl-Fisher titration, dynamic vapor sorption analysis, thermogravimetric-infrared spectroscopic analysis (TG-IR), residual solvent gas chromatography (see: https://www.restek.com/Technical-Resources/Technical-Library/Pharmaceutical/pharm_A005), 1H-NMR (see: https://en.wikipedia.org/wiki/Proton_nuclear_magnetic_resonance) etc.

Thus, in one embodiment, a solid state form of (17-β)-3-Oxoandrost-4-en-17-yl dodecanoate is provided wherein the solid state (17-β)-3-Oxoandrost-4-en-17-yl dodecanoate has one or more advantageous properties compared to other forms, such as chemical properties, crystalline, or polymorphic purity, increased crystallinity, flowability, solubility, dissolution rate, bioavailability, morphology or crystal habit, specific surface and pycnometric density, bulk/tap density, stability (e.g., such as chemical stability as well as thermal and mechanical stability with respect to polymorphic conversion), stability towards hydration and/or storage stability, a lower degree of hygroscopicity, low content of residual solvent(s) and advantageous processing and handling characteristics such as compressibility and bulk density. In the specific aspect of this embodiment, the solid state (17-β)-3-Oxoandrost-4-en-17-yl dodecanoate in this disclosure is a crystalline form. In further aspect, the solid state (17-β)-3-Oxoandrost-4-en-17-yl dodecanoate is useful for administration to a human. In one aspect, the solid state (17-β)-3-Oxoandrost-4-en-17-yl dodecanoate is a specific crystalline form characterized by an analytical techniques known in the ordinary skilled artisan (e.g., substantially similar to that characterized in the Examples and Figures by XRD and DSC).

In one aspect, the solid state (17-β)-3-Oxoandrost-4-en-17-yl dodecanoate found here has two endothermic transition peaks, that can represent change of a kind of crystalline form to a different form of solid state or phase changes (e.g., solid to liquid). FIG. 1 displays a first cycle heat enthalpy change plot for the solid state form of (17-β)-3-Oxoandrost-4-en-17-yl dodecanoate measured by differential scanning calorimetry as disclosed herein. In another aspect, one small endothermic peak showing at 35 to 45° C. in FIG. 1 can be a glass transition peak, which can be a stable solid form to a meta-state solid from (e.g., amorphous form). In further aspect, one small endothermic peak showing at 35 to 45° C. in FIG. 1 can be a lattice-form transition peak, which can be a crystalline form to a different crystalline from. In an aspect, the other large endothermic peak showing at 45 to 70° C. represents the melting point (e.g., the phase change from solid state to liquid state) of the solid state (17-β)-3-Oxoandrost-4-en-17-yl dodecanoate disclosed herein as determined by differential scanning calorimetry. In one aspect, the solid state (17-β)-3-Oxoandrost-4-en-17-yl dodecanoate is a crystalline form having a melting point in the range of 45 to 70° C., 50 to 70° C., or 50 to 65° C. as determined by differential scanning calorimetry. In one aspect, the solid state (17-β)-3-Oxoandrost-4-en-17-yl dodecanoate is a crystalline form having a melting point in the specific range of 51 to 63° C. as determined by differential scanning calorimetry as shown in See FIG. 1.

Figure 2:
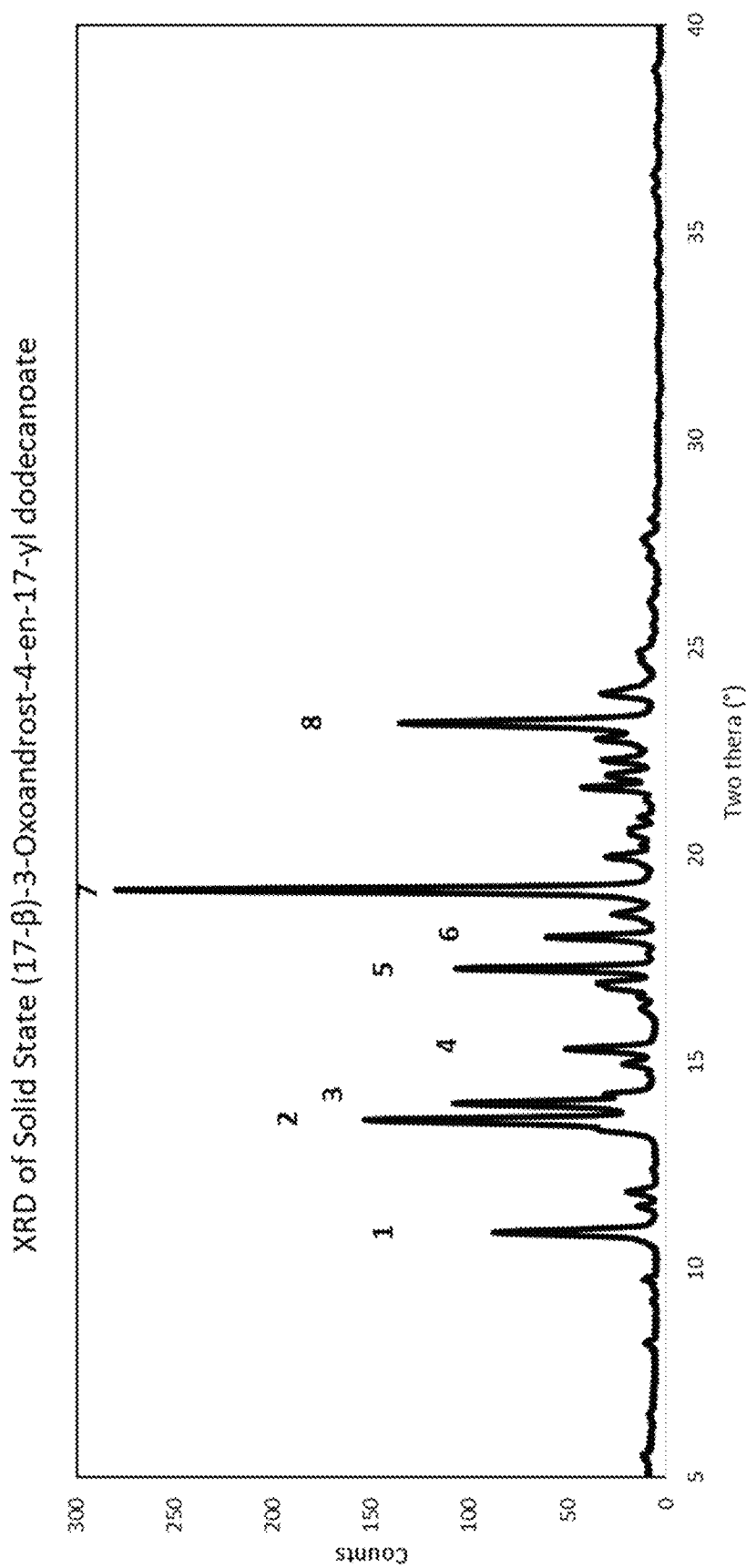
FIG. 2 shows a result of an XRD measure for a solid state (17-β)-3-Oxoandrost-4-en-17-yl dodecanoate as disclosed herein with 8 distinguishable peaks for a crystalline structure.

In one aspect, the solid state (17-β)-3-Oxoandrost-4-en-17-yl dodecanoate is a crystalline form having at least 1, 2, 3, 4, 5, 6 or more distinguished peaks as determined by XRD corresponding to those in FIG. 2. In one aspect, the solid state (17-β)-3-Oxoandrost-4-en-17-yl dodecanoate is a crystalline form which is not milled or is milled, micronized, or nanosized. In one aspect, the particle size of the solid state (17-β)-3-Oxoandrost-4-en-17-yl dodecanoate has a $d_{50}$ of greater than 1000 μm, from 355 to 1000 μm, from 180 to 355 μm, from 125 to 180 μm, from 90 to 125 μm, from 1 to 90 μm, or less than 1 μm. In one aspect, the solid state (17-β)-3-Oxoandrost-4-en-17-yl dodecanoate has particle size distribution of less than 200 nm, from 200 to 500 nm, from 500 to 1000 nm, from 1 to 50 μm, from 50 μm to 250 μm, from 250 μm to 500 μm, from 500 μm to 1000 μm, or greater than 1000 μm. In one aspect, the particle size of the solid state (17-β)-3-Oxoandrost-4-en-17-yl dodecanoate has a $D_{10}$, $D_{50}$, or $D_{90}$ that is less than 200 nm, from 200 to 500 nm, from 500 to 1000 nm, from 1 to 50 μm, from 50 to 250 μm, from 250 to 500 μm, from 500 to 1000 μm, or greater than 1000 μm. In one aspect, the release profile of the (17-β)-3-Oxoandrost-4-en-17-yl dodecanoate does not change substantially as a function of storage time.

Production of Different Forms of (17-β)-3-Oxoandrost-4-en-17-yl dodecanoate in a Pharmaceutical Composition from the Solid State Described herein are different solid state forms of (17-β)-3-Oxoandrost-4-en-17-yl dodecanoate created by compositions with any excipients or carriers (e.g., solubilizers, surfactants, additives, and so on). The identification of different forms of (17-β)-3-Oxoandrost-4-en-17-yl dodecanoate yields improvement related to physical, chemical, pharmacokinetic, and pharmacodynamic properties.

A number of different forms including crystalline forms of (17-β)-3-Oxoandrost-4-en-17-yl dodecanoate may exist. A solid state crystalline form of (17-β)-3-Oxoandrost-4-en-17-yl dodecanoate having the melting point at 55 to 65° C. shown in FIG. 1 and at least 1, 2, 3, 4, 5, 6 or more distinguished peaks as determined by XRD shown in FIG. 2 described herein can be transformed to at least one of a single crystalline form, amorphous form, polymorphic crystalline form, meta-stable solid form, or liquid form of (17-β)-3-Oxoandrost-4-en-17-yl dodecanoate by making a pharmaceutical composition comprising at least one of pharmaceutically acceptable excipients, carriers, or ingredients. In specific aspect, a variety of different forms of (17-β)-3-Oxoandrost-4-en-17-yl dodecanoate in a pharmaceutical composition can be provided by methods available to the ordinary skilled artisan in view of this disclosure: see FIG. 3.

Experimental Instrumentation and Conditions for Analyzing Solid State (17-β)-3-Oxoandrost-4-en-17-yl dodecanoate A variety of techniques may be used to identify or characterize solid state (17-β)-3-Oxoandrost-4-en-17-yl dodecanoate.

Fourier Transform-Raman Spectroscopy ("FT-Raman") (see: https://www.sciencedirect.com/topics/chemistry/fourier-tansform-raman-spectroscopy#:~:text= Near%2Dinfrared%20Fourier%20Transform%20Raman, advantages%20of%20the%20optical%20interferometer.) is useful for characterizing and identifying solid state forms of (17-β)-3-Oxoandrost-4-en-17-yl dodecanoate. For example, different solid state forms of (17-β)-3-Oxoandrost-4-en-17-yl dodecanoate may be characterized using a Bruker RFS100 instrument, with Nd:YAG 1064 nm excitation, 300 mW laser power, Ge detector, using 64 scans over the range of 25-3500 $cm^{-1}$, and with 2 $cm^{-1}$ resolution. As is understood by the ordinary skilled artisan, the parameters and instrumentation for FT-Raman may be modified depending on the instrument, the solid state (17-β)-3-Oxoandrost-4-en-17-yl dodecanoate, and goal(s) of the analysis.

Another useful technique for characterization is XRD (see: https://en.wikipedia.org/wiki/Powder_diffraction). For example, XRD can be performed with a Bruker D8 Advance X-ray diffractometer with CuKα-radiation. The standard measuring conditions are e.g., tube power 40 kV/40 mA; step size 0.010° (2θ); step time 57.6 sec; scanning range 3°-40° (2θ); divergence slit 0.600 mm; antiscatter slit 4.800 mm; slit mode fixed; sample rotation speed 15.000°/min; detector LYNXEYE_XE (1D mode); goniometer radius 280.0 nm; wavelength for display 1.54060 Å. As is understood by the ordinary skilled artisan, the parameters and instrumentation for XRD may be modified depending on the instrument, the solid state (17-β)-3-Oxoandrost-4-en-17-yl dodecanoate and goal(s) of the analysis. In one embodiment, the solid state (17-β)-3-Oxoandrost-4-en-17-yl dodecanoate is crystalline or substantially crystalline as indicated by XRD. An example of an XRD spectra is shown in FIG. 2 for a crystalline from of solid state (17-β)-3-Oxoandrost-4-en-17-yl dodecanoate. FIG. 2 shows well defined peaks corresponding to the crystalline from of the solid state (17-β)-3-Oxoandrost-4-en-17-yl dodecanoate with little or no characteristics of amorphous forms of the solid state (17-β)-3-Oxoandrost-4-en-17-yl dodecanoate (as indicated by the absence of an "amorphous halo" in the spectra in the 5-30 degree 2θ range and peaks not broadened). In one aspect, the solid state (17-β)-3-Oxoandrost-4-en-17-yl dodecanoate described herein has 1, 2, 3, 4, 5, 6, 7, 8, 9, 10, 11, or 12 or more of the peaks that correspond to those in FIG.

2 that have an intensity of above 25, 50, 100, 150, or 200 counts. The intensity can be a random relative value compared to one measured from the control.

Thermogravimetric-Fourier transform Infrared Spectroscopy ("TG-FTIR") (see: https://www.eag.com/resources/appnotes/thermogravimetric-analvsis-fourier-transfer-infrared-spectroscopy-tga-ftir-services/) can also be used to characterize or analyze the solid state (17-β)-3-Oxoandrost-4-en-17-yl dodecanoate. For example, TG-FTIR can be performed with a Netzsch Thermo-Microbalance TG 209 coupled with a Bruker FT-IR Spectrometer Vector 22, using an aluminum crucible (open or with a microhole), under a nitrogen atmosphere, and e.g., at a heating rate of 10° C./min over the range of 25° C. to 350° C. As is understood by the ordinary skilled artisan, the parameters and instrumentation for TG-FTIR may be modified depending on the instrument, the solid state (17-β)-3-Oxoandrost-4-en-17-yl dodecanoate and goal(s) of the analysis.

Characterization/Analysis of a solid state (17-β)-3-Oxoandrost-4-en-17-yl dodecanoate can also be performed using Differential Scanning calorimetry ("DSC"). For example, DSC can be performed with a Perkin Elmer Differential Scanning calorimeter, using closed Pan Al crucibles, a heating rate of 10° C. $\min^{-1}$ over a range from 0° C. to 100° C. (or e.g., over a range from 5° C. to 150° C.): For example, see FIG. 1. As is understood by the ordinary skilled artisan, the parameters and instrumentation for DSC may be modified depending on the instrument, the solid state (17-β)-3-Oxoandrost-4-en-17-yl dodecanoate and goal(s) of the analysis. Thus, in yet another embodiment, the solid state (17-β)-3-Oxoandrost-4-en-17-yl dodecanoate provided herein has a melting point in the range of about 45 to 70° C., as determined by DSC. In a specific embodiment, the solid state (17-β)-3-Oxoandrost-4-en-17-yl dodecanoate provided herein has a melting point in the range of about 50 to 65° C., as determined by DSC. In a more specific embodiment, the solid state (17-β)-3-Oxoandrost-4-en-17-yl dodecanoate provided herein has a melting point in the range of about 55 to 65° C., as determined by DSC. In one aspect of this embodiment, the melting point of the solid state (17-β)-3-Oxoandrost-4-en-17-yl dodecanoate is a characteristics of solid state forms of (17-β)-3-Oxoandrost-4-en-17-yl dodecanoate: See FIG. 1.

Dynamic Vapor Sorption (DVS) (see: https://en.wikipedia.org/wiki/Dynamic_vapor_sorption) analysis is another technique for characterizing and analyzing (17-β)-3-Oxoandrost-4-en-17-yl dodecanoate. For example, DVS can be performed with a Surface Measurement Systems DVS-1 water vapor sorption analyzer. The experiments can be run by placing the sample on a quartz holder on top of a microbalance, and allowing the sample to equilibrate at 50% relative humidity (RH) before starting the pre-defined humidity program. The program can proceed e.g., in the following steps: 1 hour at 50% RH; 50% to 0% RH at a rate of 5% RH change per hour; 5 hours at 0% RH; 0% RH to 96% RH at 5% RH change per hour; 5 hours at 95% RH; 95% RH to 50% RH at a rate of 5% RH change per hour, and followed by one hour at 50% RH As is understood by the ordinary skilled artisan, the parameters and instrumentation for DVS may be modified depending on the instrument, the solid state (17-β)-3-Oxoandrost-4-en-17-yl dodecanoate and goal(s) of the analysis.

High performance liquid chromatography (HPLC) (see: https://en.wikipedia.org/wiki/High-performance_liquid_chromatography) is also useful for analyzing or characterizing (17-β)-3-Oxoandrost-4-en-17-yl dodecanoate. In some of the embodiments, the purity of crystalline forms of (17-β)-3-Oxoandrost-4-en-17-yl dodecanoate as measured by HPLC is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% based on total area under the curve as observed at a suitable wavelength e.g., about 240 nm or about 250 nm. In some embodiments, the crystalline form of (17-β)-3-Oxoandrost-4-en-17-yl dodecanoate disclosed herein is about 98.0% to 100.0% pure as measured by HPLC as area under the curve as observed at a suitable wavelength, e.g., at a wavelength of from about 200 nm to about 300 nm, e.g., about 240 nm or 250 nm.

In some of the embodiments, the purity of different forms of (17-β)-3-Oxoandrost-4-en-17-yl dodecanoate in a pharmaceutical composition as measured by HPLC is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% based on total area under the curve as observed at a suitable wavelength e.g., about 200 nm to about 300 nm, or about 240 nm to about 250 nm. In some embodiments of the invention, different forms of (17-β)-3-Oxoandrost-4-en-17-yl dodecanoate in a pharmaceutical composition is about 98.0% to 100.0% pure as measured by HPLC based on area under the curve as observed at a suitable wavelength, e.g., at a wavelength of from about 200 nm to about 300 nm, e.g., about 240 nm or 250 nm.

As is understood by the ordinary skilled artisan, solid state NMR and other techniques can be used to analyze or characterize the solid state (17-β)-3-Oxoandrost-4-en-17-yl dodecanoate and forms thereof in view of this disclosure.

Production of Different Particle Size Distributions of Solid State (17-β)-3-Oxoandrost-4-en-17-yl dodecanoate Compositions having different particles sizes or distributions of particles sizes can be produced by any suitable method. Micronization techniques can be based on friction to reduce particle size; such methods include milling, bashing and grinding. Another technique of producing different sized (17-β)-3-Oxoandrost-4-en-17-yl dodecanoate particles involves supercritical fluids where the (17-β)-3-Oxoandrost-4-en-17-yl dodecanoate is dissolved in a solvent at high temperature and pressure and the mixture is sprayed out of a nozzle, causing the formation of particles of particular sizes or within particular size ranges/distributions. Some basic supercritical fluid techniques are RESS process (Rapid Expansion of Supercritical Solutions) (see: https:/hightechextracts.com/the-scieice/rapid-expansion-of-supercritical-solution/#:~:text=Rapid%20Expansion%20of%20Super-critical%20Solution%20(RESS)%20is%20used%20generally%20to, solution%20through%20an%20expansion%20nozzle.), the SAS method (Supercritical Anti-Solvent) (see: http://hpp.u-va.es/technology/formulation/supercritical-antisolvent-sas/#:~:text=The%20Super-critical%20Anti%20Solvent%20technique.solution%20with%20supercritical%20carbon%20dioxide.) and the PGSS method (Particles from Gas Saturated Solutions) (see: https://hightechextracts.com/the-science/particles-from-gas-saturated-solutions/#:~:text=Particles%20from%20Gas%20Saturated%20Solutions%20(PGSS)%20is%20a%20technique%20for, of%20CO2%20at%20moderate%20pressures.).

Particle Size Distribution and Morphology Analysis

Particle size distribution of solid state (17-β)-3-Oxoandrost-4-en-17-yl dodecanoate particles can be analyzed by a number of techniques. For example, particle size distribution can be analyzed by photon correlation spectroscopy (PCS) (see: https://www.sciencedirect.com/topics/chemical-engineering/photon-correlation-spectroscopy): e.g., Malvern ZetaSizer 2000 HS (Malvern Instruments, Malvern, UK). The measuring mode applied can be e.g., Contin-Auto mode. PCS yields the mean diameter of the bulk population (z-average) and a polydispersity index (PI) ranging from 0 (monodisperse) through 0.10-0.20 (relatively monodisperse) to >0.5 for a broad size distribution. The measuring range of PCS is approximately 3 nm 3 μm. As is understood by the ordinary skilled artisan, the parameters and instrumentation for PCS may be modified depending on the instrument, the solid state (17-β)-3-Oxoandrost-4-en-17-yl dodecanoate and goal(s) of the analysis.

Figure 4:
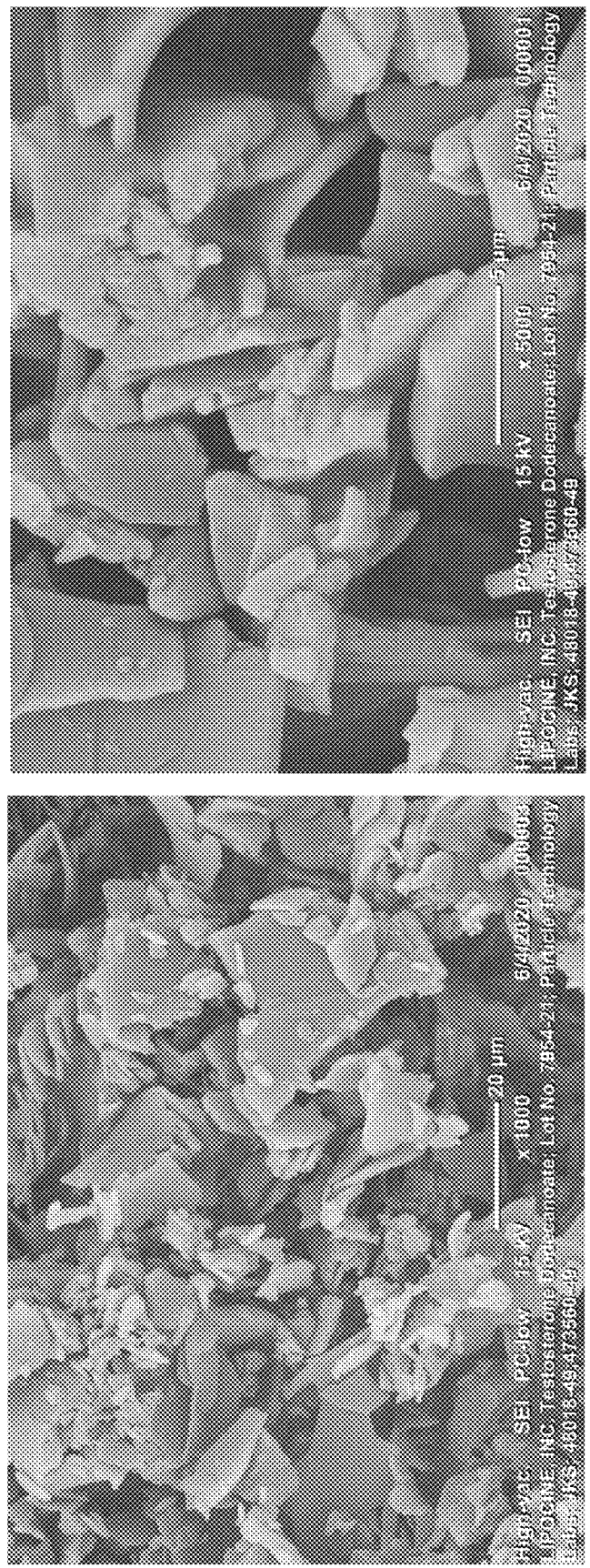
FIG. 4 shows two microscopic images with 20 μm and 5 μm scales of particles of the solid state (17-β)-3-Oxoandrost-4-en-17-yl dodecanoate used for a pharmaceutical composition or dosage form described herein, wherein said particles of the solid state (17-β)-3-Oxoandrost-4-en-17-yl dodecanoate has a specific shape, such as flat thin panel shape.

Particles of solid state (17-β)-3-Oxoandrost-4-en-17-yl dodecanoate can also be visually analyzed by Scanning Electron Microscopy (SEM) (see: https://en.wikipedia.org/wiki/Scanning_electron_microscope). Solid particles are deposited on metallic stubs then placed in liquid nitrogen and dried under vacuum. The metal stubs are coated uniformly with gold or palladium. All samples are examined for morphology and surface properties using a scanning electron microscope (e.g., Joel, SEM, JSM-25 SII, Tokyo, Japan). Particle size, polydispersity index and zeta potential can be initially measured by a laser particle size analyzer (Submicron Particle Size Analyser 90 plus, Brookhaven Instrument Co., Holtsville, N.Y., USA). An aliquot of solid state (17-β)-3-Oxoandrost-4-en-17-yl dodecanoate particles can be diluted with e.g., 3 ml of deionized water. The diluted (17-β)-3-Oxoandrost-4-en-17-yl dodecanoate samples are loaded into a 4 ml cuvette and the particle size and zeta potential measurement can be conducted at ambient temperature. For example, particles of the solid state (17-β)-3-Oxoandrost-4-en-17-yl dodecanoate characterized as shown in FIGS. 1 and 2 were measured by a scanning electron microscope. FIG. 4 shows the solid state (17-β)-3-Oxoandrost-4-en-17-yl dodecanoate particles exist as one or more crystallites, grains, and particles with a shape of flat thin panel. As shown in FIG. 4, those size ranges over one or more of about less than 1 μm, about 1-5 μm and about 5-50 μm. As is understood by the ordinary skilled artisan, the parameters and instrumentation for electron microscopy may be modified depending on the instrument, the solid state (17-β)-3-Oxoandrost-4-en-17-yl dodecanoate and goal(s) of the analysis.

The crystallite sizes of the solid state (17-β)-3-Oxoandrost-4-en-17-yl dodecanoate disclosed here, which agglomerate to particles of the solid state (17-β)-3-Oxoandrost-4-en-17-yl dodecanoate as seen in FIG. 4, can also be estimated by XRD e.g., by applying the Sherrer equation (see: https://en.wikipedia.org/wiki/Scheffer_equation) where the size of crystallites agglomerated to build particles of the solid state (e.g., crystal particles or crystallites) can be calculated, in a solid to the broadening of a peak in a diffraction pattern. Typically, particles are made from agglomeration of grains, which are agglomerated from many crystallites of the solid state. Based on XRD diffractogram shown in FIG. 4, the mean crystallite size of the solid state (17-β)-3-Oxoandrost-4-en-17-yl dodecanoate disclosed here was measured about 50 nm with standard deviation of about 7 nm. The mean crystallite size was measured using Scherrer equation as:

$$D = \frac{\kappa \times \lambda}{\beta \times \cos(\theta)}$$

wherein D is the crystallite size of the ordered domains, κ is a dimensionless Scherrer constant (=0.9), λ is the X-ray wavelength (=0.15406 nm), β is the line broadening at half the maximum intensity (FWHM) in radians for each peak, and θ is the peak position in 2θ. For example, Table 1 summarizes the crystallite sizes measured from each peak (8 distinguishable peaks) as shown in FIG. 2 using the Scherrer equation.

TABLE 1

Crystallite size measured using Scherrer equation based on peaks in XRD (FIG. 2)

| Peak ID | Peak position (2θ) | FWHM (θ) | Crystallite size (nm) |
|---|---|---|---|
| 1 | 10.9 | 0.17 | 46.9 |
| 2 | 13.6 | 0.17 | 47.1 |
| 3 | 14.0 | 0.14 | 57.2 |
| 4 | 15.3 | 0.19 | 42.2 |
| 5 | 17.3 | 0.14 | 57.4 |
| 6 | 18.0 | 0.15 | 53.6 |
| 7 | 19.2 | 0.13 | 60.2 |
| 8 | 23.2 | 0.19 | 42.7 |
| Mean | | 0.16 | 51.1 |
| SD | | 0.023 | 7.4 |

Release Profile of the Solid State (17-β)-3-Oxoandrost-4-en-17-yl dodecanoate

In one embodiment, the release profile (e.g., a profile comprising 2, 3, 4, 5, or 6 or more time points each at least 5, 10, or 15 minutes apart or a single time point) of the solid state (17-β)-3-oxoandrost-4-en-17-yl dodecanoate found here does not change substantially as a function of storage time. Additionally, the release amount of the solid state crystalline (17-β)-3-oxoandrost-4-en-17-yl dodecanoate is less than 10%, 9%, 8%, 7%, 6%, or 5% up to at least 60 min, 120 min, 180 min, 240 min, 360 min, 24 hours, or 48 hours in a USP type 2 apparatus at 100 rpm in about 1000 mL 8% Triton X-100 solution in water at a specific temperature e.g., 20.0, 37.0 or 40.0° C. (±0.5). In one aspect, the release profile of the solid (17-β)-3-Oxoandrost-4-en-17-yl dodecanoate does not substantially change over a period of 1, 2, 3, 4, 5, 6, 7, 8, 9, 10, 11, 12, 13, 14, 15, or 16 weeks. In one aspect, the release profile of the solid state (17-β)-3-Oxoandrost-4-en-17-yl dodecanoate does not substantially change over a period of 1, 2, 3, 4, 5, 6, 7, 8, 9, 10, 11, 12, 13, 14, 15, or 16 months. In one aspect, the release test is performed using a USP type 2 apparatus at 100 rpm in about 1000 mL 8% Triton X-100 solution in water at a specific temperature e.g., 20.0, 37.0 or 40.0° C. (±0.5). In one aspect, a release profile that does not substantially change over a period of time refers to a release profile that changes by less than plus/minus 50%, 40%, 30%, 20%, or 10% or less of the amount of (17-β)-3-Oxoandrost-4-en-17-yl dodecanoate released at one or more specific time point under specific conditions.

Pharmaceutical Compositions Comprising or Prepared from the Solid State (17-β)-3-Oxoandrost-4-en-17-yl dodecanoate The pharmaceutical compositions and dosage forms (e.g. capsule or tablet) described herein comprising or prepared from the solid state (17-β)-3-Oxoandrost-4-en-17-yl dodecanoate can include a variety of pharmaceutically acceptable carriers known in the common art. Non-limiting examples of components that can be included as components of the pharmaceutical carrier include lipophilic surfactants, hydrophilic surfactants, triglycerides, fatty acid (C8 to C22), fatty acid glycerides (mono-, di-, tri-, or a combination thereof), additives or a combination thereof.

In one embodiment, the pharmaceutical composition or dosage form comprising or prepared from the solid state (17-β)-3-Oxoandrost-4-en-17-yl dodecanoate is as described herein. In an aspect, the pharmaceutical composition or dosage form is prepared from solid state crystalline (17-β)-3-Oxoandrost-4-en-17-yl dodecanoate. In another aspect, the pharmaceutical composition or dosage form is prepared from specific crystalline forms of solid state (17-β)-3-Oxoandrost-4-en-17-yl dodecanoate. In yet another aspect, the pharmaceutical composition or dosage form is prepared from the crystalline form of the solid state (17-β)-3-Oxoandrost-4-en-17-yl dodecanoate as characterized by DSC and XRD as shown in FIGS. 1, 2, and 4.

In another embodiment, the crystalline form of the solid state (17-β)-3-Oxoandrost-4-en-17-yl dodecanoate can be transformed to amorphous, substantially amorphous, partially amorphous, or amorphous-like forms in the pharmaceutical composition or dosage formulation post processes for making the compositions or dosage formulations with pharmaceutically acceptable carriers. Amorphous-like refers to one of physical states of (17-β)-3-Oxoandrost-4-en-17-yl dodecanoate in a dosage form or pharmaceutical composition in which a substantial amount of the (17-β)-3-Oxoandrost-4-en-17-yl dodecanoate is not in a structured crystalline form (e.g., dissolved or dispersed in a solvent). In another specific aspect of this embodiment, the solid state (17-β)-3-Oxoandrost-4-en-17-yl dodecanoate in the pharmaceutical composition or dosage form can be semi-solid forms or substantially free of crystalline forms. In further aspect of this embodiment, the solid state (17-β)-3-Oxoandrost-4-en-17-yl dodecanoate in the pharmaceutical composition or dosage form can be partially maintained with the same crystalline forms as intact.

In yet another aspect, the pharmaceutical composition or dosage form is prepared from crystalline forms of the solid state (17-β)-3-Oxoandrost-4-en-17-yl dodecanoate and the pharmaceutical composition comprises amorphous or amorphous-like solid state (17-β)-3-Oxoandrost-4-en-17-yl dodecanoate. In yet another aspect, the pharmaceutical composition or dosage form is prepared from crystalline forms of the solid state (17-β)-3-Oxoandrost-4-en-17-yl dodecanoate and the pharmaceutical composition comprises substantially free of amorphous solid state (17-β)-3-Oxoandrost-4-en-17-yl dodecanoate. In yet another aspect, the pharmaceutical composition or dosage form is prepared from crystalline forms of the solid state (17-β)-3-Oxoandrost-4-en-17-yl dodecanoate and the pharmaceutical composition comprises solubilized (17-β)-3-Oxoandrost-4-en-17-yl dodecanoate.

In one embodiment, the pharmaceutical composition or unit dosage form comprising or prepared from the solid state (17-β)-3-Oxoandrost-4-en-17-yl dodecanoate has improved release properties as compared to the release from the crystalline forms of the solid state (17-β)-3-Oxoandrost-4-en-17-yl dodecanoate without any carriers or excipients. According to this embodiment, a pharmaceutical composition or unit dosage form comprising or prepared from the solid state (17-β)-3-Oxoandrost-4-en-17-yl dodecanoate releases more (17-β)-3-Oxoandrost-4-en-17-yl dodecanoate than do crystalline forms of the solid state (17-β)-3-Oxoandrost-4-en-17-yl dodecanoate release at a specified time point (e.g., 1 min, 2 min, 3 min, 4 min, 5 min, 6 min, 7 min, 8 min, 9 min, 10 min, 11 min, 12 min, 15 min, 20 min, 25 min, 30 min, 35 min, 45 min, 60 min, 75 min, 90 min, 105 min, 120 min, 180 min, and 240 min.) in a USP Type 2 apparatus in about 1000 mL 8% Triton X100 solution in water at a specific temperature (e.g., 20.0, 37.0 or 40.0° C. (±0.5)) at 100 rpm. Releasing more (17-β)-3-Oxoandrost-4-en-17-yl dodecanoate from the pharmaceutical composition or unit dosage form refers to releasing more than 10%, 20%, 30%, 40%, 50%, 60%, 70%, 80%, 90% or 100% or more than the crystalline forms of solid state (17-β)-3-Oxoandrost-4-en-17-yl dodecanoate in the dissolution aqueous media (e.g., 8% Triton X100 solution in water).

In one embodiment, the pharmaceutical composition or unit dosage form having (or made from) the solid state (17-β)-3-Oxoandrost-4-en-17-yl dodecanoate has a release profile (e.g., single time point or multiple time points) of (17-β)-3-Oxoandrost-4-en-17-yl dodecanoate that does not change substantially as a function of storage time as measured using a USP type 2 apparatus in about 1000 mL 8% Triton X100 solution in water at specific temperature (e.g., 20.0, 37.0 or 40.0° C. (±0.5)) at 100 rpm. In one aspect, the release profile does not substantially change over a period of 1, 2, 3, 4, 5, 6, 7, 8, 9, 10, 11, 12, 13, 14, 15, or 16 weeks. In one aspect, the release profile does not substantially change over a period of 1, 2, 3, 4, 5, 6, 7, 8, 9, 10, 11, 12, 13, 14, 15, or 16 months. In one aspect, a release profile that does not substantially change over a period of time refers to a release profile that changes by less than plus/minus 50%, 40%, 30%, 20%, or 10% or less of the amount of (17-β)-3-Oxoandrost-4-en-17-yl dodecanoate released at one or more specific time point under specific conditions.

In one embodiment, the unit dosage form or pharmaceutical composition as described herein comprising, or prepared from the solid state (17-β)-3-Oxoandrost-4-en-17-yl dodecanoate and a pharmaceutically acceptable carrier, wherein the dosage form or pharmaceutical composition releases 20% or more (17-β)-3-Oxoandrost-4-en-17-yl dodecanoate as measured with a USP Type 2 apparatus having 1000 mL 8% Triton X100 solution in water at thirty minutes at a specific temperature at 100 RPM than an equivalent release amount of crystalline solid state (17-β)-3-Oxoandrost-4-en-17-yl dodecanoate without any excipient or carrier that does not release more than 1% of the (17-β)-3-Oxoandrost-4-en-17-yl dodecanoate amount as measured with a USP Type 2 apparatus having 1000 mL 8% Triton X100 solution in water at thirty minutes, is provided.

In some embodiments, the pharmaceutically acceptable carrier of the composition can include a lipophilic additive. Non-limiting examples of lipophilic additives can include lipophilic surfactants, mono, di, or triglycerides, tocopherol, tocopherol succinate, tocopherol acetate, tocopherol derivatives, a sterol, a phytosterol and combinations thereof. In one embodiment, the lipophilic additive can include a fatty acid or fatty acid glyceride. In another embodiment, the lipophilic additive can include the fatty acid glyceride which can be a monoglyceride, a diglyceride, a triglyceride or mixtures thereof. Non-limiting examples of fatty acid glycerides that can be used in the oral pharmaceutical compositions and dosage forms of the present invention include monoglycerides and/or diglycerides derived from sources such as maize oil, poppy seed oil, safflower oil, sunflower oil, borage seed oil, peppermint oil, coconut oil, palm kernel oil, castor oil, and mixtures thereof. In a specific embodiment, the pharmaceutical composition or dosage form thereof, comprises one or more maize oil, poppy seed oil, safflower oil, sunflower oil, borage seed oil, peppermint oil, coconut oil, palm kernel oil, castor oil, or combination thereof. In another embodiment, the composition includes one or more triglycerides. In one aspect, the lipophilic additive is a C8-C22 saturated fatty acid (or has 1, 2, or 3 unsaturations on ester chain), a mono-, di-, or triglyceride thereof (including mixtures), or a combination thereof. In a more specific aspect, the C8-C22 fatty acid is caprylic acid, capric acid, lauric acid, myristic acid, palmitic acid, stearic acid, palmitoleic acid, sapienic acid, oleic acid, elaidic acid, vaccenic acid, linoleic acid, or linoelaidic acid. In another specific aspect, the mono-, di-, or triglyceride is a glyceride of caprylic acid, capric acid, lauric acid, myristic acid, palmitic acid, stearic acid, palmitoleic acid, sapienic acid, oleic acid, elaidic acid, vaccenic acid, linoleic acid, or linoelaidic acid or a combination thereof.

In another embodiment, the lipophilic additive can include a lipophilic surfactant.

As used herein a lipophilic surfactant is considered when it has a Hydrophilic-Lipophilic Balance (HLB) value of 10 or less. Various lipophilic surfactants can be used including, but not limited to mono-, di-glycerides of fatty acids like glyceryl monolinoleate (e.g. MAISINE 35-1), mono- and di glycerides of caprylic-capric acid (e.g. CAPMUL MCM), glyceryl monooleate, mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g. LABRAFIL M 2125 CS), PEG-6 almond oil (e.g. LABRAFIL M 1966 CS), PEG-6 apricot kernel oil (e.g. LABRAFIL M 1944 CS), PEG-6 olive oil (e.g. LABRAFIL M 1980 CS), PEG-6 peanut oil (e.g. LABRAFIL M 1969 CS), PEG-6 hydrogenated palm kernel oil (e.g. LABRAFIL M 2130 BS), PEG-6 palm kernel oil (e.g. LABRAFIL M 2130 CS), PEG-6 triolein (e.g. LABRAFIL M 2735 CS), PEG-8 corn oil (e.g. LABRAFIL WL 2609 BS), PEG-20 corn glycerides (e.g. CROVOL M40), PEG-20 almond glycerides (e.g. CROVOL A40), lipophilic polyoxyethylene-polyoxypropylene block co-polymers (e.g. PLURONIC L92, L101, L121 etc.); propylene glycol fatty acid esters, such as propylene glycol monolaurate (e.g. Lauroglycol FCC), propylene glycol ricinoleate (e.g. Propymuls), propylene glycol monooleate (e.g. Myverol P-O6), propylene glycol dicaprylate/dicaprate (e.g. CAPTEX 200), and propylene glycol dioctanoate (e.g. CAPTEX 800), propylene glycol monocaprylate (e.g. CAPRYOL 90); propylene glycol oleate (e.g. LUTROL OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g. ARLACEL 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (e.g. ARLACEL 20), sorbitan monopalmitate (e.g. Span-40), sorbitan monooleate (e.g. Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, and the like, and mixtures thereof. It is important to note that some lipophilic surfactants may also function as the solubilizer component of the compositions and oral dosage forms.

In one embodiment, the lipophilic surfactant can be selected from the group consisting of glyceryl monolinoleate (e.g. MAISINE 35-1), mono- and di glycerides of caprylic, capric acid (e.g. CAPMUL MCM), glyceryl monooleate, propylene glycol mono caprylate, propylene glycol oleate, propylene glycol monostearate, propylene glycol monolaurate, propylene glycol mono-oleate, propylene glycol dicaprylate/dicaprate, sorbitan monooleate, PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, sorbitan monolaurate (e.g. ARLACEL 20), sorbitan monopalmitate, sorbitan monooleate, sorbitan monostearate, sorbitan tristearate, sorbitan monolaurate, sorbitan monopalmitate, sorbitan monooleate, sorbitan trioleate, sorbitan sesquioleate, sorbitan tristearate, sorbitan monoisostearate, and combinations thereof. It should be noted that the combinations of two or more lipophilic surfactants from the same or different classes therein are also within the scope of this invention and are together can be referred to as the lipophilic surfactant, unless otherwise stated.

In embodiments of the present invention, the oral pharmaceutical compositions or dosage forms (e.g. capsule or tablet) can include a hydrophilic additive. In one embodiment, hydrophilic additive is selected from the group consisting of hydrophilic surfactants, e.g., celluloses—such as hydroxypropyl celluloses with low molecular weight, low viscosity types (e.g. METHOCEL E5, E6, E10 E15, LV100 etc. grades) and hydroxypropyl celluloses having higher molecular weight, medium to high viscosity (e.g. METHOCEL K4M, K15M, K100M etc.); polyvinylpyrrolidones (e.g. KOLLIDON k17, K30 etc.); polyvinyl acetates and combinations thereof.

In one embodiment, the hydrophilic additive can be a hydrophilic surfactant. A hydrophilic surfactant is considered when it has an HLB value of greater than 10. Non-limiting examples of hydrophilic surfactants include non-ionic surfactants, ionic surfactants and zwitterionic surfactants. Specifically the hydrophilic surfactants suitable for the current invention include, but not limited to, alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol and the like. It should be noted that the combinations of two or more hydrophilic surfactants from the same or different classes are within the scope of this invention and are together can be referred to as the hydrophilic surfactant unless explicitly specified. In one embodiment, the hydrophilic additive can be a hydrophilic surfactant. Non-limiting examples of hydrophilic surfactants can include PEG-8 caprylic/capric glycerides, lauroyl macrogol-32 glyceride, stearoyl macrogol glyceride, PEG-40 hydrogenated castor oil, PEG-35 castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, and mixtures thereof.

In some embodiments, surfactants utilized in the pharmaceutical compositions described herein include sterols and derivatives of sterols. In various embodiments, these surfactants are hydrophilic or lipophilic. Examples of hydrophilic sterol surfactants are lanosterol PEG-24 cholesterol ether (e.g. SOLULAN C-24, Amerchol), PEG-30 soya sterol (e.g. Nikkol BPS-30, from Nikko), PEG-25 phyto sterol (e.g. Nikkol BPSH-25 from Nikko), PEG-30 cholestanol (e.g. Nikkol DHC, from Nikko). Examples of lipophilic sterol surfactants are cholesterol, sitosterol, phytosterol (e.g. GENEROL series from Henkel), PEG-5 soya sterol (e.g. Nikkol BPS-S, from Nikko), PEG-10 soya sterol (e.g. Nikkol BPS-10 from Nikko), PEG-20 soya sterol (e.g. Nikkol BPS-20 from Nikko).

In one embodiment, the pharmaceutical composition or unit dosage form includes an additive as described in the following paragraphs.

Suitable additives utilized in various embodiments described herein include, by way of non-limiting example, adsorbing agents, anti-adherents, anticoagulants, antifoaming agents, antioxidants, anti-caking agents, anti-static agents, binders, bile acids, bufferants, bulking agents, chelating agents, coagulants, colorants, co-solvent, opaquants, congealing agents, coolants, cryoprotectants, diluents, dehumidifying agents, desiccants, desensitizers, disintegrants, dispersing agents, enzyme inhibitors, glidants, fillers, hydrating agent, super disintegrants, gums, mucilages, hydrogen bonding agents, enzymes, flavorants, humectants, humidifying agents, lubricant oils, ion-exchange resins, lubricants, plasticizers, pH modifying agents, preservatives, solidifying agent, solvents, solubilizers, spreading agent sweeteners, stabilizers, surface area enhancing agents, suspending agent, thickeners, viscosity increasing agents, waxes, solidifier, and mixtures thereof.

In one embodiment, the oral pharmaceutical composition or the dosage form comprises or is prepared from solid state (17-β)-3-Oxoandrost-4-en-17-yl dodecanoate and a pharmaceutically acceptable carrier. In another embodiment, the compositions or the dosage form of the current invention includes solid state (17-β)-3-Oxoandrost-4-en-17-yl dodecanoate and a pharmaceutically acceptable carrier, wherein the solid state (17-β)-3-Oxoandrost-4-en-17-yl dodecanoate is not solubilized at 30° C., or above 30° C., or at a temperature range above 30° C., including 30° C. to about 40° C. In one aspect, the unit dosage form is a hard gel or soft gel capsule or a tablet.

Methods of Use for Treatment of Disease

The pharmaceutical compositions or unit dosage forms comprising or prepared from the solid state (17-β)-3-Oxoandrost-4-en-17-yl dodecanoate have a number of methods for use.

Subjects that can be treated by administration of pharmaceutical compositions and unit dosage forms of the present disclosure (e.g., comprising or prepared from solid state (17-β)-3-Oxoandrost-4-en-17-yl dodecanoate) can be any mammal (e.g., a human male or female) in need thereof. In particular, in one embodiment, the human male may be at least 14 years of age. In another embodiment, the human male is an adult of at least age 16, 18, or 20. In another embodiment, the human male is an adult of at least age 21, 23, or 25. In another embodiment, the human male is an adult of at least age 30. In a further embodiment, the subject can be an adult male of at least age 50. In yet a further embodiment, the subject can be an adult male of at least age 60. Subjects that can be treated by pharmaceutical compositions and unit dosage forms of the present disclosure (e.g., comprising or prepared from the solid state (17-β)-3-Oxoandrost-4-en-17-yl dodecanoate characterized as shown in FIGS. 1, 2, and 4) can be any human female in need thereof. In particular, in one embodiment, the human female may be at least 14 years of age. In another embodiment, the human female is an adult of at least age 30. In a further embodiment, the subject can be an adult female of at least age 50. In a further embodiment, the subject can be an adult female who has deficient endogenous serum testosterone levels. In a further embodiment, the subject can be an adult female who has undergone unilateral or bilateral oophorectomy. In yet a further embodiment, the subject can be an adult female who has undergone unilateral or bilateral oophorectomy. In yet another embodiment, the subject can be a post-menopausal woman. In an additional aspect, the subjects having diseases related to lack of therapeutically effective testosterone levels, such as, but no limited to, hypogonadism (e.g., testosterone deficiency or absence of testosterone), liver disease or lung disease related to steatosis, inflammatory or fibrotic cytokines, chemokines, enzymes, or biomarkers can be treated with the pharmaceutical compositions or formulations prepared from or comprising the solid state (17-β)-3-Oxoandrost-4-en-17-yl dodecanoate in this disclosure.

As discussed above, the present invention also provides for a method of treating a human subject in need of testosterone therapy is provided. The method can include the steps of administering any of the pharmaceutical compositions or dosage forms (e.g., capsule or tablet) disclosed herein. The pharmaceutical compositions and the dosage forms of the present invention can be used to treat any condition associated with testosterone deficiency, including complete absence, of endogenous testosterone in male or female subjects. Examples of conditions associated with testosterone deficiency that can be treated using the dosage forms (e.g., capsule or tablet) and/or compositions of the present invention include, but are not limited to, congenital or acquired primary hypogonadism, hypogonadotropic hypogonadism, cryptorchidism, bilateral torsion, orchitis, vanishing testis syndrome, orchidectomy, Klinefelter's syndrome, post castration, eunuchoidism, hypopituitarism, endocrine impotence, infertility due to spermatogenic disorders, impotence, male sexual dysfunction (MSD) including conditions such as premature ejaculation, erectile dysfunction, decreased libido, and the like, micropenis and constitutional delay, penile enlargement, appetite stimulation, testosterone deficiency associated with chemotherapy, testosterone deficiency associated with toxic damage from alcohol, testosterone deficiency associated with toxic damage from heavy metal, osteoporosis associated with androgen deficiency, and combinations thereof.

Other conditions that can be treated by the compositions and dosage forms disclosed herein include idiopathic gonadotropin, LHRH (luteinizing hormone-releasing hormone) deficiency, or pituitary hypothalamic injury from tumors, trauma, or radiation. Typically, these subjects have low serum testosterone levels but have gonadotropins in the normal or low range. In one embodiment, the compositions or oral dosage forms may be used to stimulate puberty in carefully selected males with clearly delayed puberty not secondary to a pathological disorder. In another embodiment, the compositions and oral dosage forms may be used in female-to-male transsexuals in order to maintain or restore male physical and sexual characteristics including body muscle mass, muscle tone, bone density, body mass index (BMI), enhanced energy, motivation and endurance, restoring psychosexual activity etc. In some embodiments, pharmaceutical compositions and unit dosage forms of the present disclosure (e.g., prepared from or comprising the solid state (17-β)-3-Oxoandrost-4-en-17-yl dodecanoate disclosed here) can be useful in providing hormonal male contraception. In some embodiments, pharmaceutical compositions and unit dosage forms of the present disclosure (e.g., prepared from or comprising the solid state (17-β)-3-Oxoandrost-4-en-17-yl dodecanoate in this disclosure) can be used to provide treatment of one or more symptoms associated with female sexual dysfunction, anorgasmia, osteoarthritis, hormonal male contraception. Additionally, pharmaceutical compositions and unit dosage forms of the present disclosure (e.g., prepared from or comprising the solid state (17-β)-3-Oxoandrost-4-en-17-yl dodecanoate in this finding) can be used to treat and/or improve the patient related outcomes including the quality of life and wellbeing of the subjects suffering from deficiency of endogenous testosterone. In some embodiments, pharmaceutical compositions and unit dosage forms of the present disclosure (e.g., prepared from or comprising the solid state (17-β)-3-Oxoandrost-4-en-17-yl dodecanoate in this disclosure) can be used to treat or improve the symptoms of subjects suffering from conditions such as carcinoma, sarcoma, melanoma, lymphoma, leukemia, an end-stage condition related to liver disease, an end-stage condition related to lung disease, an end-stage condition related to kidney disease, an end-stage condition related to musculoskeletal system disease, an end-stage condition related to cardiovascular disease, an end-stage condition related to blood disease, an end-stage condition related to endocrine gland disease, an end-stage condition related to gastrointestinal disease, an end-stage condition related to skin disease, an end-stage condition related to genital organ disease, an end-stage condition related to central nervous system disease, hepatic fibrosis, hepatic inflammation, hepatic steatosis, non-alcoholic steatohepatitis (NASH), non-alcoholic fatty liver disease (NAFLD), pre/post liver transplant, cirrhosis, primary biliary cholangitis (PBC), lung disease affecting the interstitium, interstitial lung disease (ILD), pneumonia, idiopathic pulmonary fibrosis (IPF), muscle mass wasting, cachexia, sarcopenia, frailty, type 1 diabetes, type 2 diabetes, hyperglycemia, glucose intolerance, hypogonadism, hypogonadotropic hypogonadism, metabolic syndromes, visceral adiposity, obesity, impaired wound healing, large waist, and hereditary angioedema.

The following examples are provided to promote a clearer understanding of certain embodiments of this disclosure and are in no way meant as a limitation thereon.

Example 1: Preparation of Solid State
(17-β)-3-Oxoandrost-4-en-17-yl dodecanoate A non-limiting exemplary synthetic scheme for producing a solid state (17-β)-3-Oxoandrost-4-en-17-yl dodecanoate as disclosed herein and is outlined in more detail below. The (17-β)-3-Oxoandrost-4-en-17-yl dodecanoate can be produced utilizing the generalized scheme set forth below:

1) (17-β)-Hydroxy-4-Androsten-3-one (0.1 mol) is weighed and placed into a 1000 mL 4N RB flask containing a stir bar.
2) Pyridine (160 mL) is added to the flask.
3) The flask is placed in an ice-water bath and fitted with a nitrogen inlet, addition funnel, thermocouple, and stopper. Stirring and nitrogen flow are started.
4) The funnel is charged with a solution of acid chloride (1.56 equiv. e.g., lauroyl chloride) in heptane (160 mL), then fitted with an adapter connected to a bubbler.

5) The contents of the funnel are added dropwise over 30-40 min (Note: the internal temperature increases 5-7° C. during the addition.)
6) When the dropwise addition is complete, the bath is removed and stirring is continued.
7) After 1 hour, the reaction mixture is transferred to a large separatory funnel and diluted with heptane (1000 mL) (Note: TLC at 1 hour indicates a complete reaction).
8) The heptane solution is washed successively with 800 mL portions of: cold water (2×), 0.05 N NaOH, saturated NaHCO$_3$ (2×), water, brine, then dried over anhydrous Na$_2$SO$_4$ (~50 g). Then concentrated to dryness (rotavap/ T$_{bath}$≤30° C.).

Example 2: Preparation of Solid State
(17-β)-3-Oxoandrost-4-en-17-yl dodecanoate
Crystals A reaction mixture or product of Example 1 (or material produced by another route) can be transferred into water, ethanol, or methanol (or any other appropriate solvent) and allowed to crystallize. The crystalline mass can be filtered by suction, washed with water, dried over phosphorous pentoxide and re-crystallized from another solvent (although this step is not necessary) e.g., oleic acid, hexane, heptanes, etc.

Example 3: Differential Scanning Calorimetry of
Solid State (17-β)-3-Oxoandrost-4-en-17-yl
dodecanoate This example demonstrates that the solid state (17-β)-3-Oxoandrost-4-en-17-yl dodecanoate has a distinct melting point as determined using a differential scanning calorimeter. An appropriate amount of the crystalline forms of the solid state (17-β)-3-Oxoandrost-4-en-17-yl dodecanoate was placed in a closed Pan Al crucible of a differential scanning calorimeter instrument and was heated from 0 to 100° C. The result is shown in the first heating cycle (FIG. 1), which shows two endothermic transition peaks for the solid state (17-β)-3-Oxoandrost-4-en-17-yl dodecanoate disclosed here at about 30-40° C. and about 50-65° C. In a specific aspect, the melting point of the specific crystalline forms of the solid state (17-β)-3-Oxoandrost-4-en-17-yl dodecanoate is identified at 51 63° C. based on the DSC results.

Example 4: XRD Crystallography of Solid State
(17-β)-3-Oxoandrost-4-en-17-yl dodecanoate The solid state (17-β)-3-Oxoandrost-4-en-17-yl dodecanoate is crystalline or substantially crystalline as indicated by XRD as shown in an example of an XRD spectra in FIG. 2 for the crystalline forms of the solid state (17-β)-3-Oxoandrost-4-en-17-yl dodecanoate. FIG. 2 displays well defined peaks corresponding to the crystalline forms of the solid state (17-β)-3-Oxoandrost-4-en-17-yl dodecanoate with little or no amorphous forms of (17-β)-3-Oxoandrost-4-en-17-yl dodecanoate (as indicated by the absence of an "amorphous halo" in the spectra in the 5-30° of 2θ range and no broadening of the peaks).

Figure 3:
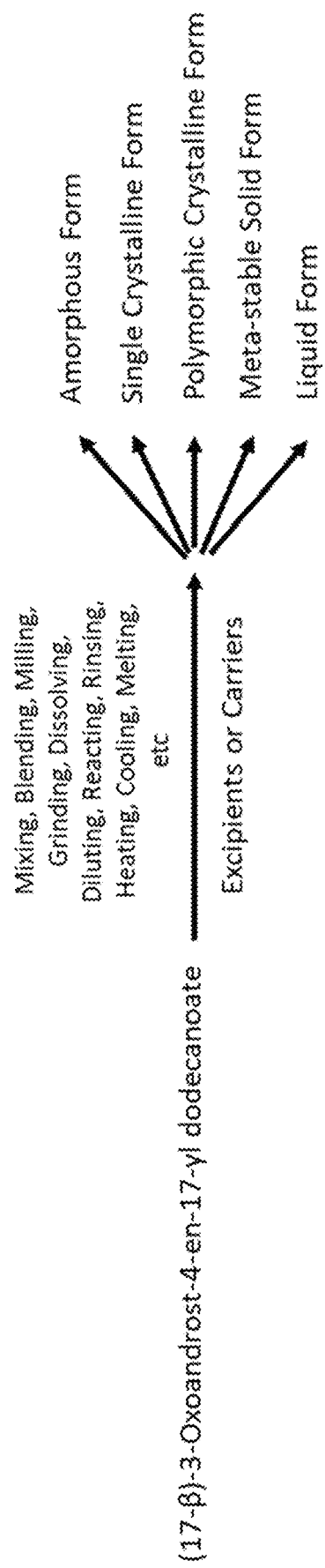
FIG. 3 shows general formulation processes for producing a variety of different forms of (17-β)-3-Oxoandrost-4-en-17-yl dodecanoate in a pharmaceutical composition or dosage form to improve physical, chemical, pharmacokinetic, and pharmacodynamic properties for enhancing bioavailability as disclosed herein.

Example 5: Pharmaceutical Compositions or
Dosage Forms Having a Variety of Different Forms
of (17-β)-3-Oxoandrost-4-en-17-yl dodecanoate
Prepared by Typical Formulation Methods Pharmaceutical compositions or dosage forms described herein are formulated or prepared from a specific crystalline forms of the solid state (17-β)-3-Oxoandrost-4-en-17-yl dodecanoate characterized by DSC and XRD, as shown in FIGS. 1 and 2. Pharmaceutical compositions or dosage forms disclosed herein are prepared from the specific solid state (17-β)-3-Oxoandrost-4-en-17-yl dodecanoate and at least one of pharmaceutical acceptable carriers by any suitable process including one or more steps of, by way of non-limiting example, agglomeration, air suspension chilling, air suspension drying, balling, coacervation, comminution, compression, pelletization, cryopelletization, encapsulation, extrusion, granulation, homogenization, inclusion complexation, lyophilization, nanoencapsulation, melting, mixing, molding, grinding, milling, pan coating, solvent dehydration, sonication, spheronization, spray chilling, spray congealing, spray drying, or the like, as shown in FIG. 3, known to the skilled artisan or developed in view of the teachings herein.

It is understood that the above-described compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. A crystalline form of (17-β)-3-Oxoandrost-4-en-17-yl dodecanoate having an XRD pattern comprising at least five peaks selected from the group of angles of 10.9±0.2, 13.6±0.2, 14.0±0.2, 15.3±0.2, 17.3±0.2, 18.0±0.2, 19.2±0.2, and 23.2±0.2 measured relative to two-theta (2θ).

2. The (17-β)-3-Oxoandrost-4-en-17-yl dodecanoate of claim 1, wherein said at least five peaks comprises at least one of 6 peaks, 7 peaks, and more than 7 peaks.

3. The (17-β)-3-Oxoandrost-4-en-17-yl dodecanoate of claim 1, wherein said crystalline form comprises a plurality of crystallites ranging in size from about 40 nm to about 60 nm.

4. The (17-β)-3-Oxoandrost-4-en-17-yl dodecanoate of claim 1, wherein said (17-β)-3-Oxoandrost-4-en-17-yl dodecanoate has a melting point in the range of about 51° C. to about 63° C.

5. A pharmaceutical composition comprising a crystalline form of (17-β)-3-Oxoandrost-4-en-17-yl dodecanoate having an XRD pattern comprising at least five peaks selected from the group of angles of 10.9±0.2, 13.6±0.2, 14.0±0.2, 15.3±0.2, 17.3±0.2, 18.0±0.2, 19.2±0.2, and 23.2±0.2 measured relative to two-theta (2θ) and at least one additive.

6. A pharmaceutical composition for an oral or injectable administration comprising a crystalline form of (17-β)-3-Oxoandrost-4-en-17-yl dodecanoate having an XRD pattern comprising at least five peaks selected from the group of angles of 10.9±0.2, 13.6±0.2, 14.0±0.2, 15.3±0.2, 17.3±0.2, 18.0±0.2, 19.2±0.2, and 23.2±0.2 measured relative to two-theta (2θ) and at least one additive.

7. The pharmaceutical composition of claim 6, wherein said pharmaceutical composition for oral administration further comprises at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule, and wherein said pharmaceutical composition for injectable administration further comprises at least one of an intravenous injectable, an intramuscular injectable, a subcutaneous injectable, an intradermal injectable, an intraspinal injectable, an intrathecal injectable, and an intra-arterial injectable comprising at least one of an implant, a solution, a suspension, an emulsion, a microemulsion, a nanoemulsion, a gel, a liposome, and a pellet.

8. The (17-β)-3-Oxoandrost-4-en-17-yl dodecanoate of claim 1, wherein said (17-β)-3-Oxoandrost-4-en-17-yl dodecanoate has a melting point in the range of about 51° C. to about 63° C., and wherein said crystalline form comprises a plurality of crystallites ranging in size from about 40 nm to about 60 nm, and wherein said (17-β)-3-Oxoandrost-4-en-17-yl dodecanoate is in a form of at least one of a capsule and a tablet for oral administration.

9. A pharmaceutical composition comprising a crystalline form of (17-β)-3-Oxoandrost-4-en-17-yl dodecanoate having an XRD pattern comprising at least five peaks selected from the group of angles of 10.9±0.2, 13.6±0.2, 14.0±0.2, 15.3±0.2, 17.3±0.2, 18.0±0.2, 19.2±0.2, and 23.2±0.2 measured relative to two-theta (2θ) and at least one carrier, said carrier comprising at least one of a lipophilic carrier and a hydrophilic carrier.

10. The pharmaceutical composition of claim 9, wherein said at least one lipophilic carrier comprises at least one of a lipophilic surfactant and a lipophilic additive, and wherein said hydrophilic carrier comprises at least one of a hydrophilic surfactant and a hydrophilic additive.

11. The pharmaceutical composition of claim 10, wherein said at least one lipophilic carrier comprises at least one of a fatty acid, a derivative of a fatty acid, a vegetable oil, a derivative of a vegetable oil, a monoglyceride, a diglyceride, a triglyceride, a derivative of a monoglyceride, a derivative of a diglyceride, a derivative of a triglyceride, a sterol, a phytosterol, a tocopherol, a tocopherol succinate, a tocopherol acetate and a fish oil, and wherein said hydrophilic carrier comprises at least one of a polyoxyethylene hydrogenated vegetable oil, a polyoxyethylene vegetable oil, a polyethylene glycol fatty acid ester, a polyethylene glycol fatty acid monoglyceride mixture, a polyethylene glycol fatty acid diglyceride mixture, a polysorbate, a polyethylene glycol derivative of tocopherol, an alcohol, and an alcohol derivative.

12. The pharmaceutical composition of claim 11, wherein said at least one fatty acid comprises at least one of an oleic acid, a lauric acid, a stearic acid, and a derivative thereof, and wherein said vegetable oil comprises at least one of a peppermint oil, a sesame oil, a borage oil, a castor oil, a maize oil, a cottonseed oil, and a derivative thereof, and wherein said derivative of monoglyceride comprises at least one of glyceryl monolinoleate, and sorbitan mono-fatty acid, and wherein said derivative of diglyceride comprises glyceryl palmitostearate, and wherein said polyoxyethylene hydrogenated vegetable oil comprises PEG hydrogenated castor oil, and wherein said alcohol comprises at least one of ethyl alcohol and benzyl alcohol, and wherein said alcohol derivative comprises benzyl benzoate.

13. A pharmaceutical composition for treating a condition for which testosterone is needed, said composition comprising a crystalline form of (17-β)-3-Oxoandrost-4-en-17-yl dodecanoate having an XRD pattern comprising at least five peaks selected from the group of angles of 10.9±0.2, 13.6±0.2, 14.0±0.2, 15.3±0.2, 17.3±0.2, 18.0±0.2, 19.2±0.2, and 23.2±0.2 measured relative to two-theta (2θ) and at least one additive.

14. A pharmaceutical composition comprising a crystalline form of (17-β)-3-Oxoandrost-4-en-17-yl dodecanoate having an XRD pattern comprising at least five peaks selected from the group of angles of 10.9±0.2, 13.6±0.2, 14.0±0.2, 15.3±0.2, 17.3±0.2, 18.0±0.2, 19.2±0.2, and 23.2±0.2 measured relative to two-theta (2θ) and at least one additive, wherein said composition is for the treatment of at least one of carcinoma, sarcoma, melanoma, lymphoma, leukemia, end-stage to liver disease, end-stage lung disease, end-stage kidney disease, end-stage musculoskeletal system disease, end-stage cardiovascular disease, end-stage blood disease, end-stage endocrine gland disease, end-stage gastrointestinal disease, end-stage skin disease, end-stage genital organ disease, end-stage central nervous system disease, hepatic fibrosis, hepatic inflammation, hepatic steatosis, non-alcoholic steatohepatitis (NASH), non-alcoholic fatty liver disease (NAFLD), pre/post liver transplant, cirrhosis, primary biliary cholangitis (PBC), lung disease affecting the interstitium, interstitial lung disease (ILD), pneumonia, idiopathic pulmonary fibrosis (IPF), muscle mass wasting, cachexia, sarcopenia, frailty, type 1 diabetes, type 2 diabetes, hyperglycemia, glucose intolerance, hypogonadism, hypogonadotropic hypogonadism, a metabolic syndrome, visceral adiposity, obesity, impaired wound healing, large waist, and hereditary angioedema.

15. A crystalline form of (17-β)-3-Oxoandrost-4-en-17-yl dodecanoate having a) the chemical structure of an XRD pattern comprising at least five peaks selected from the group of angles of 10.9±0.2, 13.6±0.2, 14.0±0.2, 15.3±0.2, 17.3±0.2, 18.0±0.2, 19.2±0.2, and 23.2±0.2 measured relative to two-theta (2θ), b) a melting point in the range of about 51° C. to about 63° C., and c) a plurality of crystallites ranging in size from about 40 nm to about 60 nm.

16. A pharmaceutical composition comprising at least one additive and a crystalline form of (17-β)-3-Oxoandrost-4-en-17-yl dodecanoate having a) the chemical structure of an XRD pattern comprising at least five peaks selected from the group of angles of 10.9±0.2, 13.6±0.2, 14.0±0.2, 15.3±0.2, 17.3±0.2, 18.0±0.2, 19.2±0.2, and 23.2±0.2 measured relative to two-theta (2θ), b) a melting point in the range of about 51° C. to about 63° C., and c) a plurality of crystallites ranging in size from about 40 nm to about 60 nm, wherein said composition is for the treatment of at least one of carcinoma, sarcoma, melanoma, lymphoma, leukemia, end-stage liver disease, end-stage condition related to lung disease, end-stage condition related to kidney disease, end-stage musculoskeletal system disease, end-stage cardiovascular disease, end-stage blood disease, end-stage endocrine gland disease, end-stage gastrointestinal disease, end-stage skin disease, end-stage genital organ disease, end-stage central nervous system disease, hepatic fibrosis, hepatic inflammation, hepatic steatosis, non-alcoholic steatohepatitis (NASH), non-alcoholic fatty liver disease (NAFLD), pre/post liver transplant, cirrhosis, primary biliary cholangitis (PBC), lung disease affecting the interstitium, interstitial lung disease (ILD), pneumonia, idiopathic pulmonary fibrosis (IPF), muscle mass wasting, cachexia, sarcopenia, frailty, type 1 diabetes, type 2 diabetes, hyperglycemia, glucose intolerance, hypogonadism, hypogonadotropic hypogonadism, a metabolic syndrome, visceral adiposity, obesity, impaired wound healing, large waist, and hereditary angioedema, and wherein said pharmaceutical composition is formulated for at least one of oral administration and injectable administration, and wherein said pharmaceutical composition for oral administration further comprises at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule, and wherein said pharmaceutical composition for injectable administration further comprises at least one of an intravenous injectable, an intramuscular injectable, a subcutaneous injectable, an intradermal injectable, an intraspinal injectable, an intrathecal injectable, and an intra-arterial injectable comprising at least one of an implant, a solution, a suspension, an emulsion, a microemulsion, a nanoemulsion, a gel, a liposome, and a pellet.

17. The composition of claim 5, wherein said at least one additive comprises at least one of a solubilizer and a surfactant.

18. The composition of claim 6, wherein said at least one additive comprises at least one of a solubilizer and a surfactant.

19. The composition of claim 9, wherein said composition further comprises at least one solubilizer.

20. The composition of claim 13, wherein said at least one additive comprises at least one of a solubilizer and a surfactant.

21. The composition of claim 14, wherein said at least one additive comprises at least one of a solubilizer and a surfactant.

22. The composition of claim 16, wherein said at least one additive comprises at least one of a solubilizer and a surfactant.

* * * * *